(12) United States Patent
Ono

(10) Patent No.: US 7,226,564 B2
(45) Date of Patent: Jun. 5, 2007

(54) PLATE ASSEMBLY

(75) Inventor: Koichi Ono, Kawaguchi (JP)

(73) Assignee: Enplas Corporation, Saitama (JP)

( * ) Notice: Subject to any disclaimer, the term of this patent is extended or adjusted under 35 U.S.C. 154(b) by 407 days.

(21) Appl. No.: 10/626,759

(22) Filed: Jul. 21, 2003

(65) Prior Publication Data

US 2004/0071600 A1 Apr. 15, 2004

(30) Foreign Application Priority Data

| Jul. 26, 2002 | (JP) | ............................. P2002-218562 |
| Aug. 23, 2002 | (JP) | ............................. P2002-243428 |
| Jan. 20, 2003 | (JP) | ............................. P2003-010699 |
| Jan. 20, 2003 | (JP) | ............................. P2003-010772 |

(51) Int. Cl.
*B01L 3/00* (2006.01)
(52) U.S. Cl. ...................................... 422/102; 422/104
(58) Field of Classification Search ................ 422/100, 422/102–104; 204/456, 419, 420
See application file for complete search history.

(56) References Cited

U.S. PATENT DOCUMENTS

| 6,406,636 B1* | 6/2002 | Vaganov ......................... 216/2 |
| 2002/0022261 A1* | 2/2002 | Anderson et al. ......... 435/287.2 |
| 2002/0053399 A1 | 5/2002 | Soane et al. |
| 2002/0079219 A1* | 6/2002 | Zhao et al. .................. 204/451 |

FOREIGN PATENT DOCUMENTS

JP 11-58437 3/1999

OTHER PUBLICATIONS

Japanese Patent Laid-Open No. 11-58467 (published on Mar. 2, 1999).

Japanese Patent Laid-Open No. 2000-246092 (published on Sep. 12, 2000).

Japanese Patent Laid-Open No. 2000-288381 (published on Oct. 17, 2000).

* cited by examiner

*Primary Examiner*—Jill Warden
*Assistant Examiner*—Natalia Levkovich
(74) *Attorney, Agent, or Firm*—Bachman & LaPointe, P.C.

(57) ABSTRACT

A plate assembly has a plate member (1, 21, 101) having a recessed portion (3, 23, 103), and a lid member (2, 22, 102) mounted on the plate member to cover the recessed portion. A gap is formed between the plate member and the lid member around the recessed portion so as to allow a liquid to permeate the gap due to capillarity while preventing the liquid from entering the recessed portion. If the liquid is an adhesive, the lid member (2, 22) is bonded to the plate member (1, 21), the plate member having a bonded surface (4, 26) which is formed so as to surround the recessed portion (3, 23), the plate member having an adhesive relief portion (25) which is formed around the bonded surface so as to be recessed from the bonded surface, the gap being formed between the bonded surface and the lid member so as to allow the adhesive to permeate the gap due to capillarity. If the liquid may be a filler, the plate member (101) has a sealing surface (105) which is formed so as to surround the recessed portion (103), the plate member having a lid member fixing surface (107) which is separated from the sealing surface by a pass partition groove (106), the lid member (102) being fixed to the lid member fixing surface to form the gap between the sealing surface and the lid member so as to allow the filler to permeate the gap due to capillarity.

25 Claims, 32 Drawing Sheets

PLATE ASSEMBLY

BACKGROUND OF THE INVENTION

1. Field of the Invention

The present invention generally relates to a plate assembly. More specifically, the invention relates to a plate assembly capable of being widely used as a micro chip or the like (e.g. a capillary electrophoresis chip) which is used in a technical field called the integrated chemistry.

2. Description of the Prior Art

In recent years, there is known a technique called the integrated chemistry for preparing a fine groove having a width and depth of about tens to two hundreds micrometers in a micro chip of a glass or plastic, to use the fine groove as a liquid passage, a reaction vessel or a separation/purification detecting vessel, to integrate a complicated chemical system into the micro chip. According to such an integrated chemistry, a micro chip (Lab-on-chip) having a fine groove capable of being used in various tests is called a total analytical system (μ-TAS) if the use of the micro chip is limited to analytical chemistry, and the micro chip is called a micro reactor if the use of the micro chip is limited to a reaction. When various tests, such as analyses, are carried out, the integrated chemistry has advantages that the time to transport diffusible molecules is short due to its small space and that the heat capacity of a liquid phase is very small. Therefore, the integrated chemistry is noticed in the technical field wherein a micro space is intended to be utilized for carrying out analysis and chemical synthesis. Furthermore, the term "test" means a test carried out by any one or combinations of operations and means, such as analysis, measurement, synthesis, decomposition, mixing, molecular transportation, solvent extraction, solid phase extraction, phase separation, phase combination, molecular uptake, culture, heating and cooling.

In such an integrated chemistry, a capillary electrophoresis chip used in a test in the field of, e.g. biochemistry, has a fine groove or circular recessed portion having a width and depth of 10 to 200 micrometers in the chip of a glass or plastic, to use the fine groove or recessed portion as a liquid passage or reaction vessel to separate and identify a very small amount of vital materials, such as nucleic acids and proteins, and other low molecular materials, and to handle materials having a very small volume of nanoliters to picoliters. Therefore, it is required to precisely form the fine groove.

As methods for forming a fine groove (a hollow portion) in a glass or plastic, there are blow molding and lost-core methods. It is difficult for these methods to precisely form a fine groove having a cross section tens micrometers square. Therefore, there is adopted a method for forming a fine groove in a surface of a glass or plastic plate to bond a lid member (another plate) to the surface of the plate having the fine groove. As methods for bonding two plates, there are generally known ultrasonic welding, vibrating welding, laser beam welding, insert molding (see Japanese Patent Laid-Open No. 11-58467) and adhesion (see Japanese Patent Laid-Open Nos. 2000-246092 and 2000-288381).

However, in the ultrasonic welding and vibrating welding, materials to be bonded to each other are locally melted, so that there is the possibility that a hollow portion having a cross section, e.g. about tens micrometers square, may be deformed. In addition, it is required to use a special equipment to increase costs. Therefore, the ultrasonic welding and vibrating welding can not be adopted.

In the laser welding, it takes a lot of welding time when the shape of the fine groove is complicated, and it is required to use a special equipment, so that there is a problem in that production costs are increased.

In the insert molding disclosed in Japanese Patent Laid-Open No. 11-58468, a plastic plate having a fine groove is previously housed in a cavity of an injection molding die, and a film covering the fine groove is arranged on the surface of the plastic plate. Thereafter, a plastic to be formed as a lid member is injected into the cavity to form a capillary electrophoresis chip. In the insert molding, there are problems in that the shape of the die is complicated and production costs are increased.

In the adhesion, a lid member is fixed to the surface of a plate having a fine groove with an adhesive. If the lid member is simply pasted on the plate, there is some possibility that the adhesive is extruded into the fine groove so that the adhesive entering the fine groove changes the cross section of the fine groove or fills up the fine groove. However, if it is possible to prevent such troubles from being caused, it is possible to efficiently form a capillary electrophoresis chip at low costs without the need of any special equipment.

Therefore, as disclosed in Japanese Patent Laid-Open Nos. 2000-246092 and 2000-288381, there has been developed a technique wherein an energy line curable composition is used as an adhesive to irradiate a part of the adhesive other than that in a fine groove with energy lines to harden the part of the adhesive to wash and remove only the adhesive in the fine groove with a solvent. However, there are problems in that it is difficult to simply carry out such a technique in an actual production field considering productivity and that such a technique requires an expensive equipment.

SUMMARY OF THE INVENTION

It is therefore an object of the present invention to eliminate the aforementioned problems and to provide a plate assembly capable of being produced by simply bonding and fixing a lid member to a plate member having a fine groove while preventing an adhesive from entering the fine groove.

In order to accomplish the aforementioned and other objects, according to one aspect of the present invention, a plate assembly comprises: a plate member having a recessed portion; and a lid member mounted on the plate member to cover the recessed portion, wherein a gap is formed between the plate member and the lid member around the recessed portion so as to allow a liquid to permeate the gap due to capillarity while preventing the liquid from entering the recessed portion.

Furthermore, throughout the specification, the term "recessed portion" means a groove serving as a passage, a circular or rectangular recessed portion used for storage, reaction or the like, or a recessed portion having a predetermined shape required to carry out a test.

In this plate assembly, the gap may be so formed as to fill the liquid in the gap due to capillarity. The gap may also be so formed as to allow the liquid to permeate the gap due to capillarity up to a portion just above a side wall of the recessed portion. The lid member may have a through hole for injecting the liquid into a space which is defined between the plate member and the lid member and which is communicated with the recessed portion. The plate member may have an excessive liquid receiving portion for receiving therein an excessive part of the liquid. The lid member may have a through hole for feeding a sample into the recessed portion. The plate assembly may further comprise means for holding the gap so as to allow the liquid to permeate the gap due to capillarity while preventing the liquid from entering the recessed portion.

In the above described plate assembly, the liquid may be an adhesive. In this case, the lid member may be bonded to the plate member, the plate member having a bonded surface which is formed so as to surround the recessed portion, the plate member having an adhesive relief portion which is formed around the bonded surface so as to be recessed from the bonded surface, and the gap being formed between the bonded surface and the lid member so as to allow the adhesive to permeate the gap due to capillarity.

In this plate assembly, the lid member may have an adhesive injecting hole which is open to a portion of the adhesive relief portion of the plate member in the vicinity of the bonded surface. The lid member may have an adhesive injecting hole, at least a part of which is open to the adhesive relief portion of the plate member. The lid member may have an adhesive injecting hole which is open to the bonded surface on the side of an end portion of the recessed portion.

In addition, the lid member may have a protrusion, at least a part of which engages the adhesive relief portion of the plate member.

Moreover, at least one of the bonded surface of the plate member and the lid member may have a spacer protrusion which contacts the other of the bonded surface of the plate member and the lid member to form the gap between the bonded surface of the plate member and the lid member so as to allow the adhesive to permeate the gap due to capillarity. At least one of the adhesive relief portion of the plate member and the lid member may have a spacer protrusion which contacts the other of the adhesive relief portion of the plate member and the lid member to form the gap between the bonded surface of the plate member and the lid member so as to allow the adhesive to permeate the gap due to capillarity. Each of the bonded surface of the plate member and the lid member may have a spacer protrusion, and the spacer protrusion of the plate member may contact the spacer protrusion of the lid member to form the gap between the bonded surface of the plate member and the lid member so as to allow the adhesive to permeate the gap due to capillarity. At least one of the plate member and the lid member may have a plurality of spacer protrusions which contact the other of the plate member and the lid member to form the gap between the bonded surface of the plate member and the lid member so as to allow the adhesive to permeate the gap due to capillarity, and a distance between adjacent two of the plurality of spacer protrusions may increase as a distance from the recessed portion increases. In these cases, at least one of the bonded surface of the plate member and the lid member may have a protrusion which has a lower height than the gap so as not to contact the other of the bonded surface of the plate member and the lid member.

The above described plate assembly may further comprise a spacer, arranged between the plate member and the lid member, for forming the gap between the bonded surface of the plate member and the lid member so as to allow the adhesive to permeate the gap due to capillarity.

Alternatively, in the above describe plate assembly, the liquid may be a filler. In this case, the plate member may have a sealing surface which is formed so as to surround the recessed portion, the plate member having a lid member fixing surface which is separated from the sealing surface by a pass partition groove, and the lid member being fixed to the lid member fixing surface to form the gap between the sealing surface and the lid member so as to allow the filler to permeate the gap due to capillarity. The filler may be arranged between the sealing surface and the lid member.

In this plate assembly, the lid member may have a filler injecting hole, which is open to a portion of the pass partition groove of the plate member in the vicinity of the sealing surface, for injecting the filler into the pass partition groove to allow the filler to permeate the gap due to capillarity. The lid member may have a filler injecting hole, at least a part of which is open to the pass partition groove of the plate member, for injecting the filler into the pass partition groove to allow the filler to permeate the gap due to capillarity. The lid member may have a filler injecting hole, which is open to the sealing surface on the side of an end portion of the recessed portion of the plate member, for injecting the filler into the pass partition groove to allow the filler to permeate the gap due to capillarity.

In addition, at least one of the sealing surface of the plate member and the lid member may have a spacer protrusion which contacts the other of the sealing surface of the plate member and the lid member to form the gap between the sealing surface of the plate member and the lid member so as to allow the filler to permeate the gap due to capillarity. At least one of the lid member fixing surface of the plate member and the lid member may have a spacer protrusion which contacts the other of the lid member fixing surface of the plate member and the lid member to form the gap between the lid member fixing surface of the plate member and the lid member so as to allow the filler to permeate the gap due to capillarity. Each of the sealing surface of the plate member and the lid member may have a spacer protrusion, and the spacer protrusion of the plate member contacting spacer protrusion of the lid member to form the gap between the sealing surface of the plate member and the lid member so as to allow the filler to permeate the gap due to capillarity. At least one of the plate member and the lid member may have a plurality of spacer protrusions which contact the other of the plate member and the lid member to form the gap between the sealing surface of the plate member and the lid member so as to allow the filler to permeate the gap due to capillarity, and a distance between adjacent two of the plurality of spacer protrusions may increase as a distance from the recessed portion increases. In these cases, at least one of the sealing surface of the plate member and the lid member may have a protrusion which has a lower height than the gap so as not to contact the other of the sealing surface of the plate member and the lid member.

The above described plate assembly may further comprise a spacer, arranged between the plate member and the lid member, for forming the gap between the sealing surface of the plate member and the lid member so as to allow the filler to permeate the gap due to capillarity.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a plate assembly according to the present invention will be described below in detail. In each of the following preferred embodiments, a plate assembly used as a capillary electrophoresis chip will be described as an example.

First Preferred Embodiment

Figure 1:
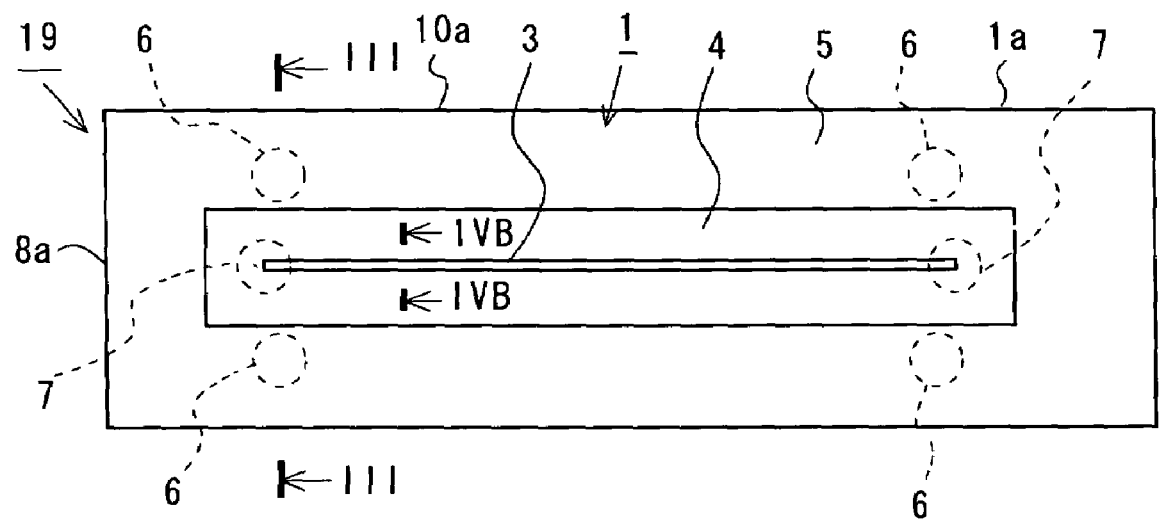
FIG. 1 is a plan view of a plate member in the first preferred embodiment of a plate assembly according to the present invention.
Figure 2:
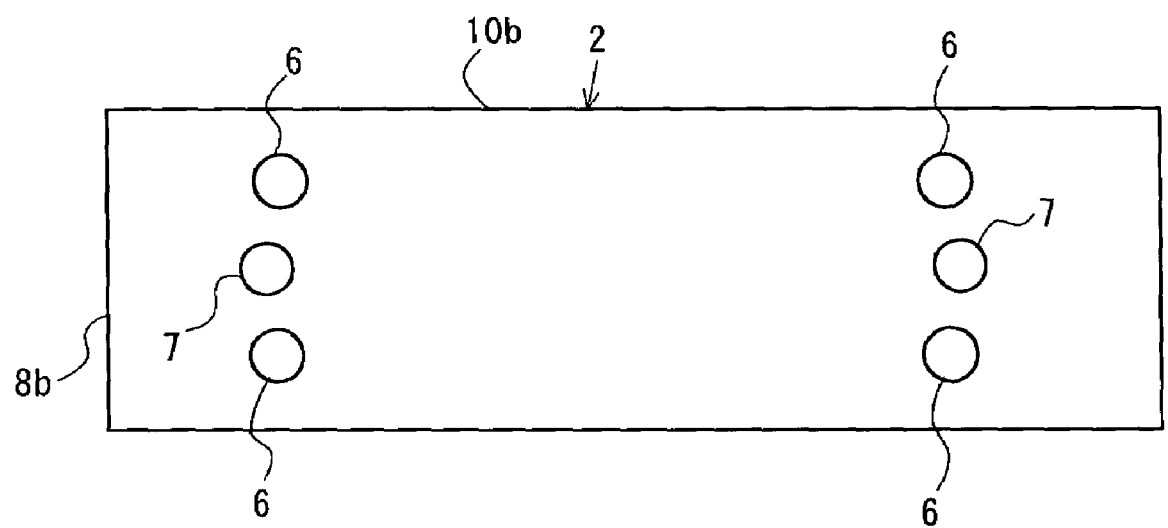
FIG. 2 is a plan view of a lid member in the first preferred embodiment of a plate assembly according to the present invention.
Figure 3:
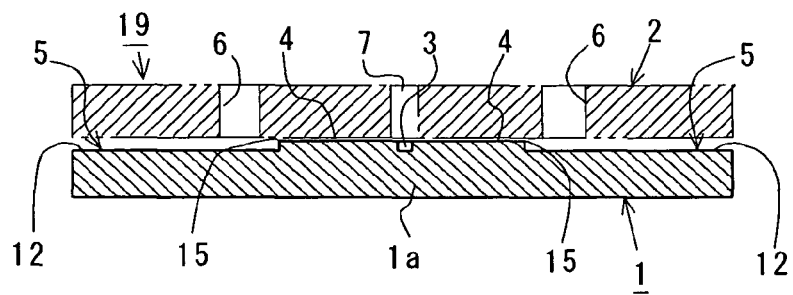
FIG. 3 is a sectional view taken along line III-III of FIG. 1.
Figure 4A:
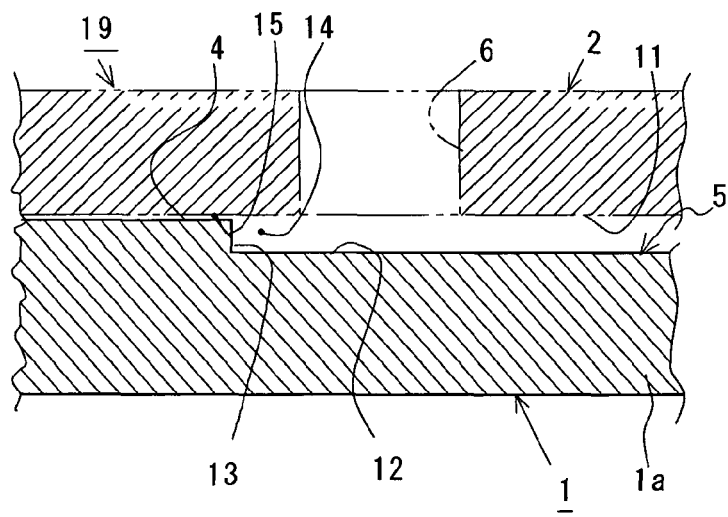
FIG. 4A is an enlarged view of a part of FIG. 3.
Figure 4B:
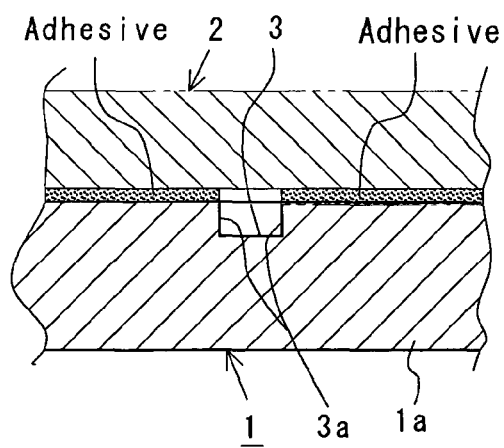
FIG. 4B is a sectional view taken along line IVB-IVB of FIG. 1.

FIGS. 1 through 4B show the first preferred embodiment of a plate assembly according to the present invention. FIG. 1 is a plan view of a plate member 1 in the first preferred embodiment. In FIG. 1, the construction of a lid member 2 bonded to the plate member 1 is also shown by dotted lines. FIG. 2 is a plan view of the lid member 2. FIG. 3 is a sectional view taken along line III-III of FIG. 1. FIG. 4A is an enlarged sectional view showing a part of FIG. 3, and FIG. 4B is a sectional view taken along line IVB-IVB of FIG. 1.

The plate member 1 and the lid member 2 are formed of, e.g. polycarbonate (PC), polymethyl methacrylate (PMMA), ultraviolet curable resin or the like, and are preferably formed of the same material. If the plate member 1 and the lid member 2 are formed of the same material, the surface charge of the plate member 1 can be the same as that of the lid member 2, so that the electroosmosis flow to a sample during electrophoresis can be uniform to cause the flow of the sample to be constant. In addition, if the plate member 1 and the lid member 2 are formed of the same material, the behavior of an adhesive toward the plate member 1 is the same as that toward the lid member 2, so that the movement of the adhesive due to capillarity is smooth.

The plate member 1 has an elongated linear fine groove (recessed portion) 3 substantially at the central portion of its plate body 1a. The fine groove 3 has a substantially square cross section (the length of one side is in the range of from 50 to 100 micrometers), and an overall length of a few centimeters. Around the fine groove 3, a bonded surface 4 having a predetermined width is formed. Around the bonded surface 4, an adhesive relief portion 5 is formed so as to be recessed from the bonded surface 4. The adhesive relief portion 5 is recessed by substantially the same depth as that of the fine groove 3. The adhesive relief portion 6 does not only serve as a non-bonded surface, but it functions as a dam serving as an adhesive collecting portion.

The lid member 2 is a plate member substantially having the same plane size as that of the plate member 1. A pair of adhesive injecting holes 6 are formed in the lid member 2 symmetrically with respect to the fine groove 3 so as to be open to the adhesive relief portion 5 on the side of one end portion of the fine groove 3, and a pair of adhesive injecting holes 6 are formed in the lid member 2 symmetrically with respect to the fine groove 3 so as to be open to the adhesive relief portion 5 on the side of the other end portion of the fine groove 3. The adhesive injecting holes 6 formed in the lid member 2 are slightly spaced from the bonded surface 4. The lid member 2 also has through holes 7 at positions corresponding to both end portions of the fine groove 3 of the plate member 1.

The plate member 1 and the lid member 2 are assembled as follows. For example, the first side 8b of the lid member 2 of FIG. 2 is aligned with the first side 8a of the plate member 1 of FIG. 1, and the second side 10b of the lid member 2 of FIG. 2 is aligned with the second side 10a of the plate member 1 of FIG. 1. In this state, the plate member 1 and the lid member 2 are held by a gripping means (not shown). Then, an adhesive is injected into the adhesive injecting holes 6. The adhesive preferably has a small coefficient of viscosity so as to be suited to utilize capillarity which will be described later. If it takes a lot of time to harden the adhesive, there is some possibility that the adhesive flowing onto the bonded surface 4 may move, so that the setting time of the adhesive is preferably short. For example, ultraviolet curable adhesive 3042 (trade name) produced by Three Bond is preferably used. Furthermore, the first side 8a and second side 10a of the plate member 1, and the first side 8b and second side 10b of the lid member 2 serve as reference surfaces when the plate member 1 and the lid member 2 are aligned with and bonded to each other. The first sides 8a and 8b are substantially perpendicular to the second sides 10a and 10b.

As shown in FIG. 4A, when the adhesive injected into the adhesive injecting holes 6 collects in a space 14, which is defined by the bottom face 11 of the lid member 2 and the surface 12 and side 13 of the adhesive relief portion 5, to reach a fine gap 15 between the bonded surface 4 of the plate member 1 and the bottom face 11 of the lid member 2, the adhesive rapidly permeates the fine gap 15 due to capillarity. At this time, as shown in FIG. 4B, since the adhesive is designed to permeate the fine gap 15 between the bonded surface 4 of the plate member 1 and the bottom surface 11 of the lid member 2 due to capillarity, the adhesive does not enter the fine groove 3, in which the gap between the plate member 1 and the lid member 2 abruptly increases, due to capillarity, and the adhesive permeates up to a portion just above the side walls 3a of the fine groove 3. Furthermore, it is considered that, if the plate member 1 and the lid member 2 are formed by the injection molding, the surface property of an injection molding die is transferred to the surfaces of the plate member 1 and lid member 2 to form the fine gap 15 of a few microns between the bonded surface 4 of the plate member 1 and the lid member 2 to cause capillarity by the fine gap 15.

If the lid member 2 is thus bonded to the plate member 1, a capillary electrophoresis chip (micro chip) 19 is formed. Then, the fine groove 3 of the capillary electrophoresis chip 19 is filled with a medium for separation, such as a buffer solution for electrophoresis or a polymer for molecular sieving, which is fed from one of the through holes 7 of the lid member 2, and a sample is fed into one end portion of the fine groove 3 from the other through hole 7 of the lid member 2. Thereafter, a high voltage is applied to both ends of the fine groove 3 to move the sample in the fine groove 3. By the difference in charge or molecular weight, a specific material is separated from the sample. The separated specific material is detected by ultraviolet absorption or fluorescence.

As described above, according to this preferred embodiment, when the lid member 2 is bonded and fixed to the plate member 1, the adhesive does not enter the fine groove 3, so that the sectional shape of the fine groove 3 is not deformed by the adhesive entering the fine groove 3. In addition, the fine groove 3 is not filled up with the adhesive entering the fine groove 3. Therefore, if the plate assembly formed by bonding the lid member 2 to the plate member 1 at a predetermined position in this preferred embodiment is used as a capillary electrophoresis chip, the movement of the sample in the fine groove 3 due to electrophoresis is not prevented by the adhesive.

According to this preferred embodiment, the adhesive can surely permeate the gap between the bonded surface 4 of the plate member 1 and the lid member 2 due to capillarity, so that the lid member 2 can be surely bonded to the plate member 1.

In addition, according to this preferred embodiment, the adhesive does not enter the fine groove 3, in which the gap between the plate member 1 and the lid member 2 abruptly increases, due to capillarity, and the adhesive permeates up to a portion just above the side walls 3a of the fine groove 3. Therefore, the sectional shape of the passage for the sample can be uniformly ensured as designed (it is possible to prevent the cross-sectional area of the passage for the sample from varying), so that the flow of the sample can be stabilized to improve the precision of analysis.

Moreover, according to this preferred embodiment, since the adhesive relief portion 5 is formed outside of the bonded surface 4, the lid member 2 can be bonded to the plate member 1 by the minimum amount of adhesive, so that the amount of adhesive to be used can be saved.

Figure 5:
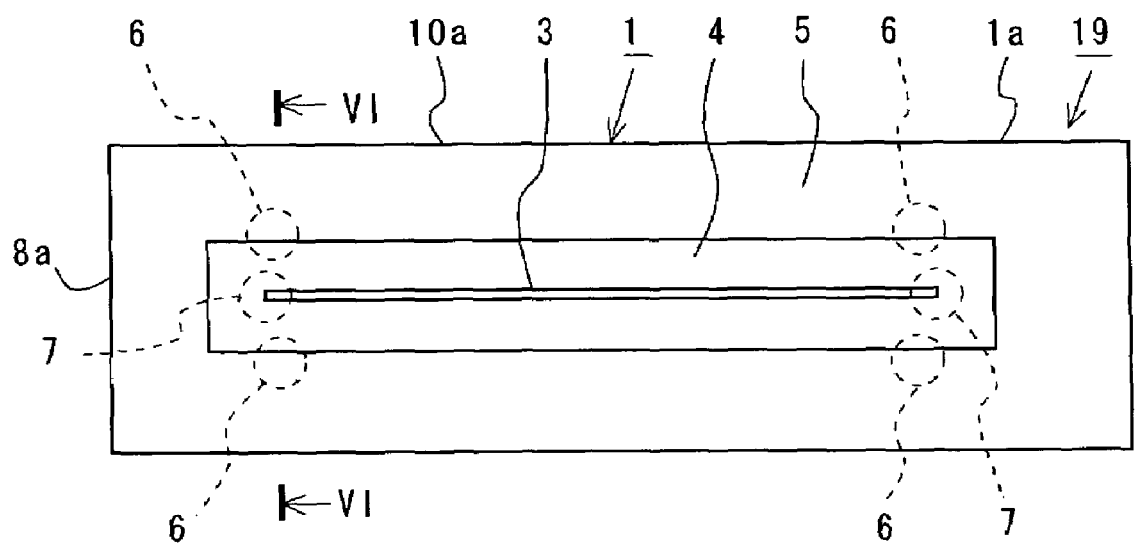
FIG. 5 is a plan view of a first modified example of the first preferred embodiment of a plate assembly according to the present invention.
Figure 6:
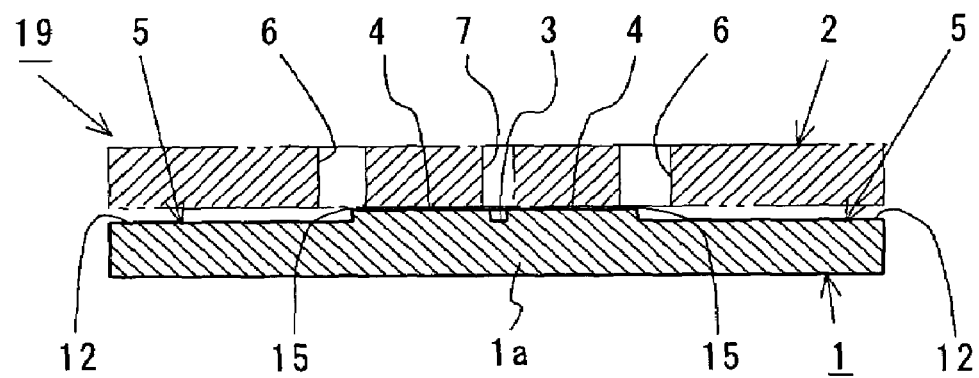
FIG. 6 is a sectional view taken along line VI-VI of FIG. 5.

FIGS. 5 and 6 show a first modified example of the first preferred embodiment of a plate assembly according to the present invention.

In this example, the construction of the plate assembly is the same as that in the first preferred embodiment, except that the positions of the adhesive injecting holes 6 are different from those in the first preferred embodiment. That is, in this example, the adhesive injecting holes 6 are open to both of the bonded surface 4 and adhesive relief portion 5 of the plate member 1.

According to this example with such a construction, if the adhesive is dropped from the adhesive injecting holes 6, excessive part of the adhesive other than part of the adhesive permeating the fine gap 15 between the bonded surface 4 of the plate member 1 and the lid member 2 due to capillarity flows into the adhesive relief portion 5 from the adhesive injecting holes 6. As a result, even if an excessive amount of adhesive is injected into the adhesive injecting holes 6, the adhesive is not pushed into the fine groove 3 by an injecting pressure. Therefore, this example can obtain the same advantageous effects as those in the above described first preferred embodiment.

Figure 7:
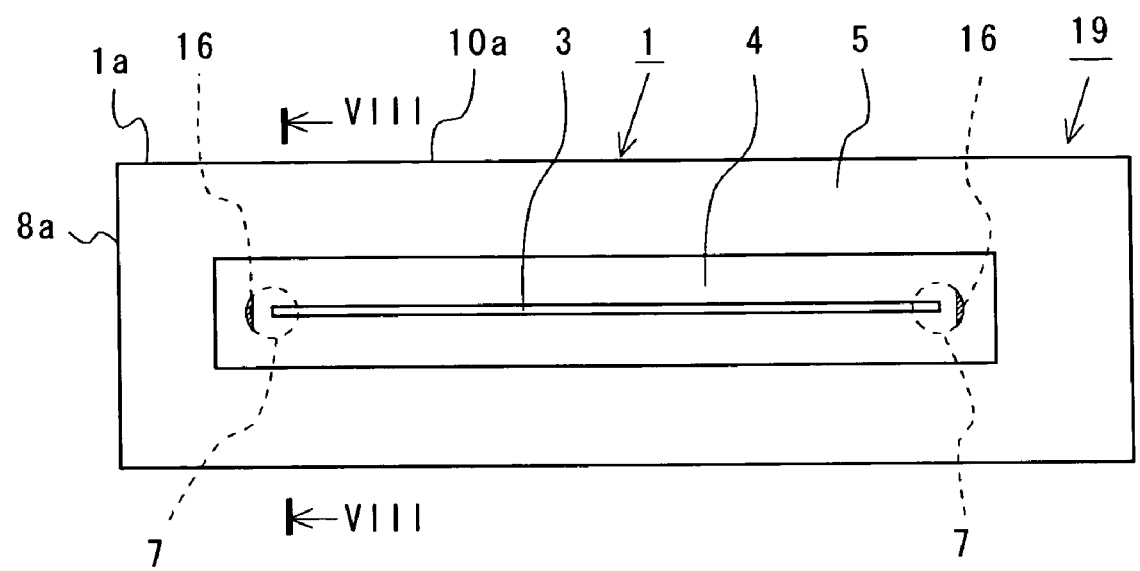
FIG. 7 is a plan view of a second modified example of the first preferred embodiment of a plate assembly according to the present invention.
Figure 8:
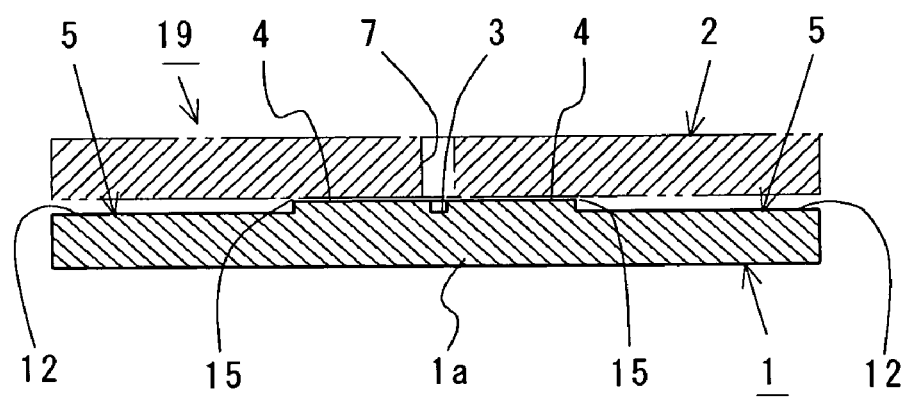
FIG. 8 is a sectional view taken along line VIII-VIII of FIG. 7.

FIGS. 7 and 8 show a second modified example of the first preferred embodiment of a plate assembly according to the present invention.

In this example, the through holes 7 of the lid member 2 open to both end portions of the fine groove 3 are also used as adhesive injecting holes. In this example, when the adhesive is dropped from the through holes 7, target dropped regions are preferably regions (regions 16 shown by slant lines in FIG. 7) which are positioned above the bonded surface 4 on the opposite side to the fine groove 3 and which extend along the walls of the through holes 7. If the adhesive is dropped in such regions, the dropped adhesive permeates the fine gap 15 between the bonded surface 4 and the lid member 2 due to capillarity, so that it is possible to prevent the adhesive from entering the fine groove 3. However, in this example, excessive part of the adhesive cannot flow into the adhesive relief portion 5, so that it is required to precisely control the amount of the adhesive to be dropped.

Figure 9:
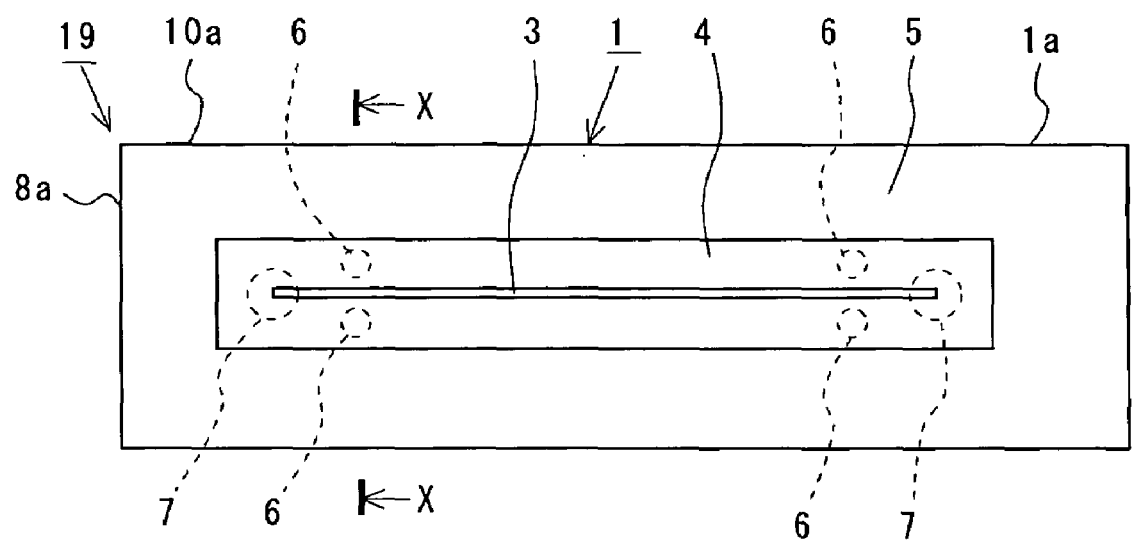
FIG. 9 is a plan view of a third modified example of the first preferred embodiment of a plate assembly according to the present invention.
Figure 10:
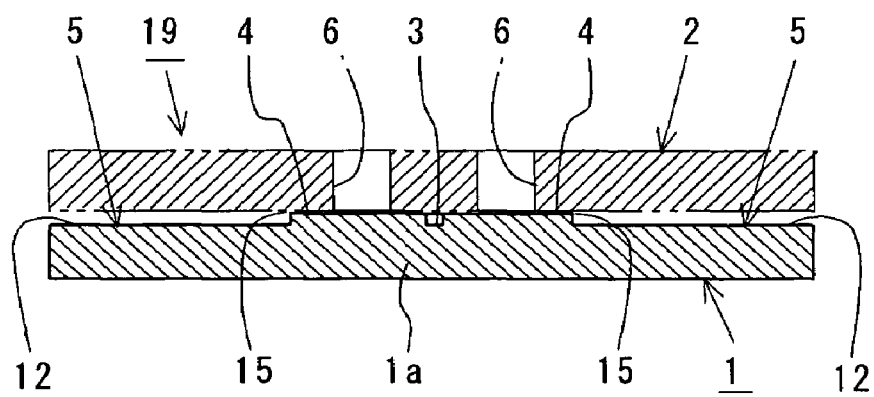
FIG. 10 is a sectional view taken along line X-X of FIG. 9.

FIGS. 9 and 10 show a third modified example of the first preferred embodiment of a plate assembly according to the present invention.

In this example, the adhesive injecting holes 6 open to the bonded surface 4 of the plate member 1 are formed in the lid member 2, and the adhesive is dropped from the adhesive injecting holes 6. Also in this case, the adhesive dropped from the adhesive injecting holes 6 permeates the fine gap 15 between the bonded surface 4 and the lid member 2 due to capillarity.

Second Preferred Embodiment

Figure 11:
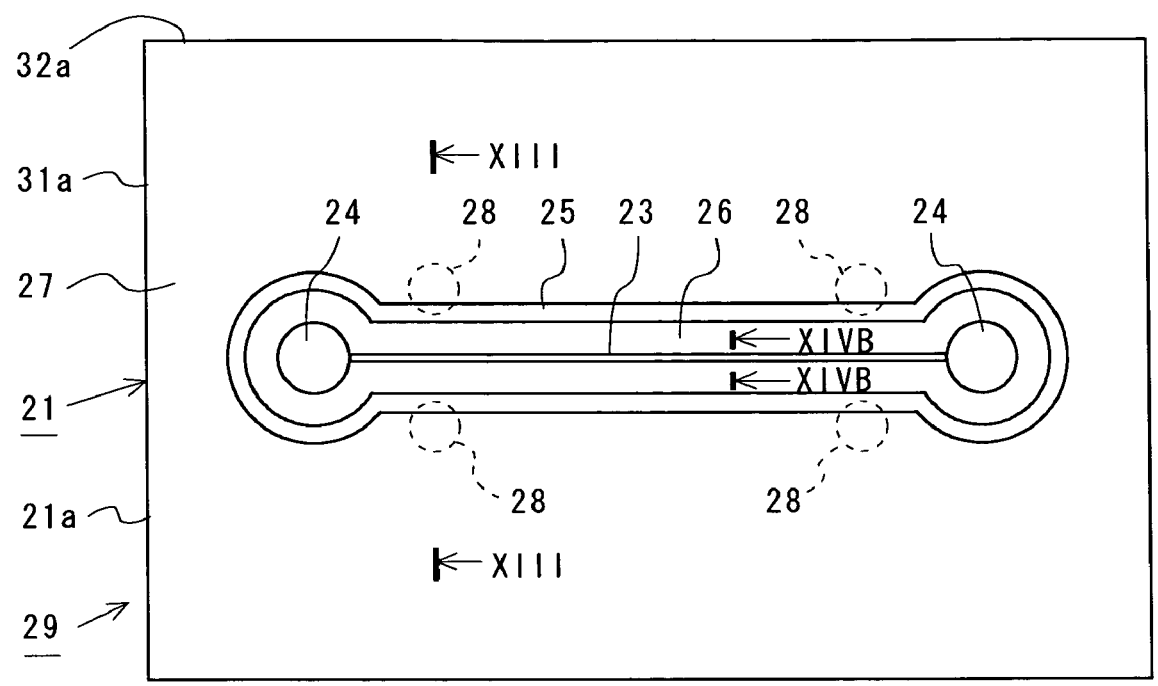
FIG. 11 is a plan view of a plate member in the second preferred embodiment of a plate assembly according to the present invention.
Figure 12:
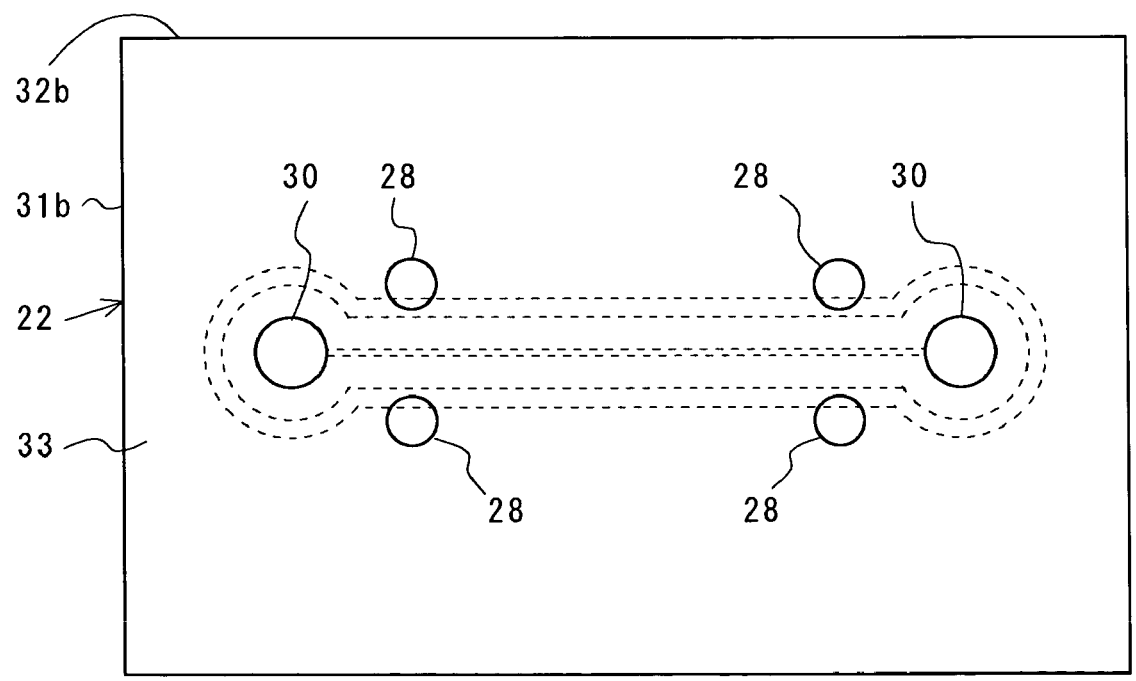
FIG. 12 is a plan view of a lid member in the first preferred embodiment of a plate assembly according to the present invention.
Figure 13:
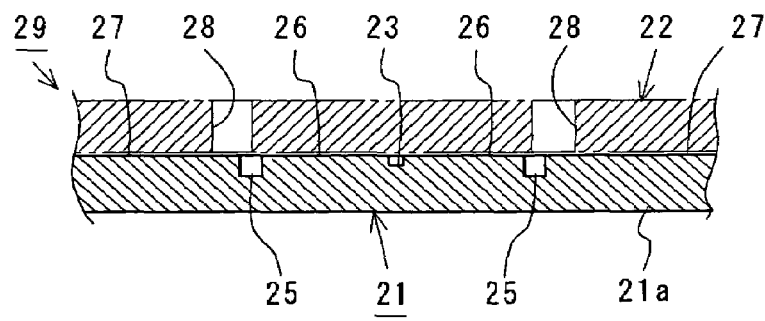
FIG. 13 is a sectional view taken along line XIII-XIII of FIG. 11.
Figure 14A:
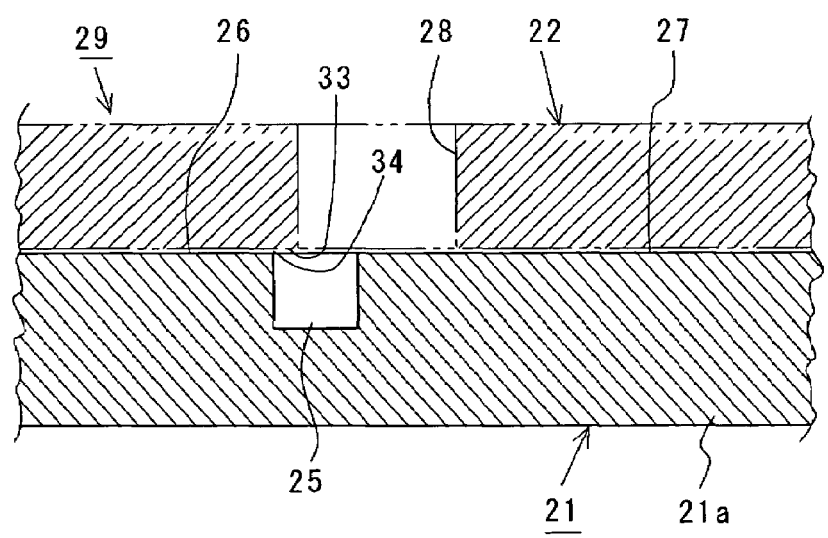
FIG. 14A is an enlarged view of a part of FIG. 13.
Figure 14B:
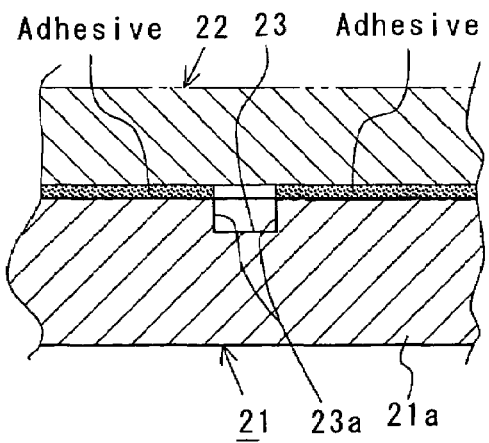
FIG. 14B is a sectional view taken along line XIVB-XIVB of FIG. 11.

FIGS. 11 through 14B show the second preferred embodiment of a plate assembly according to the present invention. FIG. 11 is a plan view of a plate member 21 in the second preferred embodiment. In FIG. 11, the construction of a lid member 22 bonded to the plate member 21 is also shown by dotted lines. FIG. 12 is a plan view of the lid member 22. FIG. 13 is a sectional view taken along line XIII-XIII of FIG. 11. FIG. 14A is an enlarged sectional view showing a part of FIG. 13, and FIG. 14B is a sectional view taken along line XIVB-XIVB of FIG. 11. Furthermore, in this preferred embodiment, the plate member 21 and the lid member 22 are formed of PC, PMMA or the like similar to the above described first preferred embodiment.

In this preferred embodiment, the plate member 21 has an elongated linear fine groove (recessed portion) 23 in its plate body 21a, and circular sample receiving holes (recessed portions) 24 on both end portions of the fine groove 23, so that the sample receiving holes 24 are communicated with the fine groove 23 (see FIG. 11). The plate member 21 also has a pass partition groove 25 serving as an adhesive relief portion which is formed so as to surround the fine groove 23 and sample receiving holes 24 apart therefrom, and a bonded surface 26 having a predetermined width between the pass partition groove 25 and the fine groove 23 and sample receiving holes 24. Around the pass partition groove 25, a butt face (surface) 27 substantially having the same height as that of the bonded surface 26 is formed. Furthermore, in this preferred embodiment, as shown in FIGS. 13 and 14B, the fine groove 23 has a square cross section, one side of which has a length of 0.3 millimeters. As shown in FIGS. 13 and 14A, the pass partition groove 25 has a square cross section, one side of which has a length of 1 millimeter.

The lid member 22 substantially has the same plane size as that of the plate member 21. A pair of adhesive injecting holes 28 are formed in the lid member 2 on the side of each of both end portions of the fine groove 23. The adhesive injecting holes 28 are arranged outside of the bonded surface 26 of the plate member 21, and part of each of the adhesive injecting holes 28 is designed to be open to the pass partition groove 25. The adhesive injecting holes 28 on the side of one end of the fine groove 23, and the adhesive injecting holes 28 on the side of the other end of the fine groove 23 are formed symmetrically with respect to the fine groove 23, respectively. The lid member 22 also has a pair of through holes 30 corresponding to the sample receiving holes 24 of the plate member 21.

According to this preferred embodiment with such a construction, it is possible to obtain the same advantageous effects as those in the above described first preferred embodiment. That is, in this preferred embodiment, the plate member 21 and the lid member 22 are assembled as follows. For example, the first sides 31a and 31b in FIGS. 11 and 12 are aligned with each other as reference surfaces, and the second sides 32b and 32b in FIGS. 11 and 12 are aligned with each other as reference surfaces. In this state, the plate member 21 and the lid member 22 are held by a gripping means (not shown). Then, an adhesive is injected into the adhesive injecting holes 28. The adhesive preferably has a small coefficient of viscosity so as to be suited to utilize capillarity which will be described later. If it takes a lot of time to harden the adhesive, there is some possibility that the adhesive flowing onto the bonded surface 26 may move, so that the setting time of the adhesive is preferably short. For example, ultraviolet curable adhesive 3042 (trade name) produced by Three Bond is preferably used. As shown in FIG. 14A, when the adhesive injected into the adhesive injecting holes 28 collects in the pass partition groove 25 to reach a fine gap 34 between the bonded surface 26 of the plate member 21 and the bottom face 33 of the lid member 22, the adhesive rapidly permeates the fine gap 34 due to capillarity. At this time, as shown in FIG. 14B, since the adhesive is designed to permeate the fine gap 34 between the bonded surface 26 of the plate member 21 and the bottom surface 33 of the lid member 22 due to capillarity, the adhesive does not enter the fine groove 23, in which the gap between the plate member 21 and the lid member 22 abruptly increases, due to capillarity, and the adhesive permeates up to a portion just above the side walls 23a of the fine groove 23. Furthermore, it is considered that, if the plate member 21 and the lid member 22 are formed by the injection molding, the surface property of an injection molding die is transferred to the surfaces of the plate member 21 and lid member 22 to form the fine gap 34 of a few microns between the bonded surface 26 of the plate member 21 and the lid member 22 to cause capillarity by the fine gap 34.

If the lid member 22 is thus bonded to the plate member 21, a capillary electrophoresis chip (micro chip) 29 is formed. Then, the fine groove 23 of the capillary electrophoresis chip 29 is filled with a medium for separation, such as a buffer solution for electrophoresis or a polymer for molecular sieving, which is fed from one of the through holes 30 of the lid member 22, and a sample is fed into one end of the fine groove 23 from the other through hole 30 of the lid member 22. Thereafter, a high voltage is applied to both ends of the fine groove 23 to move the sample in the fine groove 23. By the difference in charge or molecular weight, a specific material is separated from the sample. The separated specific material is detected by ultraviolet absorption or fluorescence.

As described above, according to this preferred embodiment, when the lid member 22 is bonded and fixed to the plate member 21, the adhesive does not enter the fine groove 23. Thus, the sectional shape of the fine groove 23 is not deformed by the adhesive entering the fine groove 3, and the fine groove 23 is not filled up with the adhesive entering the fine groove 23. Therefore, if the plate assembly formed by bonding the lid member 22 to the plate member 21 at a predetermined position in this preferred embodiment is used as a capillary electrophoresis chip, the movement of the sample in the fine groove 23 due to electrophoresis is not prevented by the adhesive.

According to this preferred embodiment, the adhesive can surely permeate the gap between the bonded surface 26 of the plate member 21 and the lid member 22 due to capillarity, so that the lid member 22 can be surely bonded to the plate member 21.

In addition, according to this preferred embodiment, the adhesive does not enter the fine groove 23, in which the gap between the plate member 21 and the lid member 22 abruptly increases, due to capillarity, and the adhesive permeates up to a portion just above the side walls 23a of the fine groove 23. Therefore, the sectional shape of the passage for the sample can be uniformly ensured as designed (it is possible to prevent the cross-sectional area of the passage for the sample from varying), so that the flow of the sample can be stabilized to improve the precision of analysis.

Moreover, according to this preferred embodiment, since the size of the pass partition groove 25 serving as the adhesive relief portion is about three times as large as that of the fine groove 23, the pass partition groove 25 is more preferably formed than the adhesion relief portion 5 arranged outside of the whole circumference of the bonded surface 4 as shown in FIG. 1 if the adhesive relief portion is tightly formed so as to be adjacent to the fine groove 23.

Figure 15:
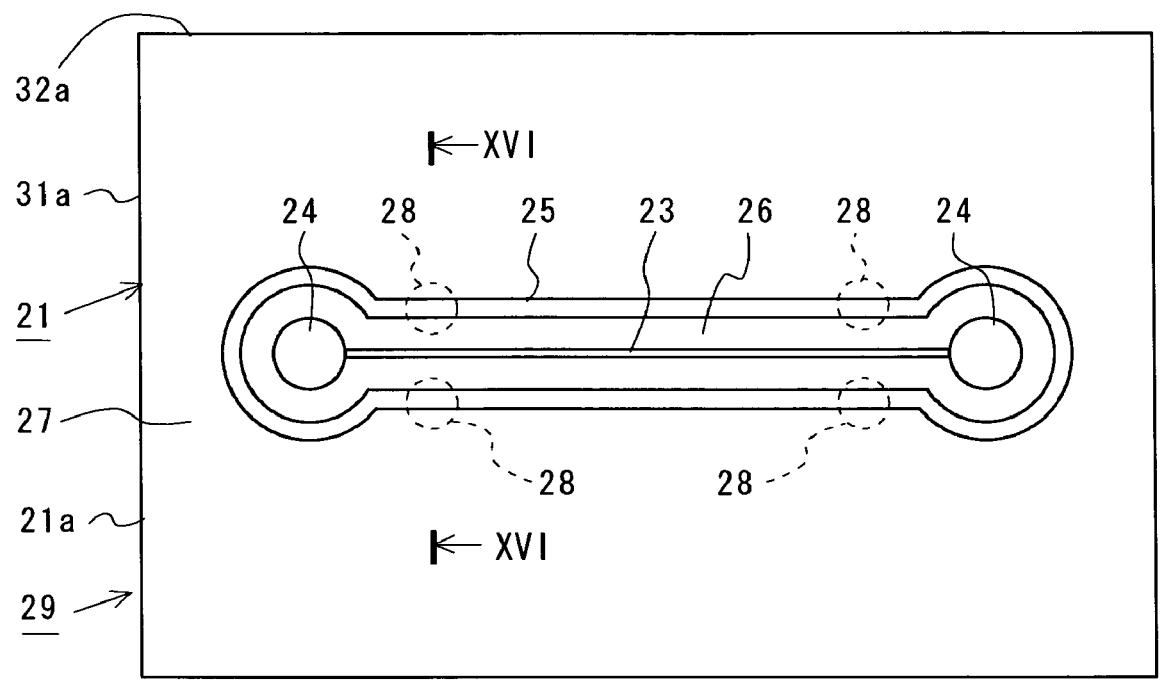
FIG. 15 is a plan view of a first modified example of the second preferred embodiment of a plate assembly according to the present invention.
Figure 16:
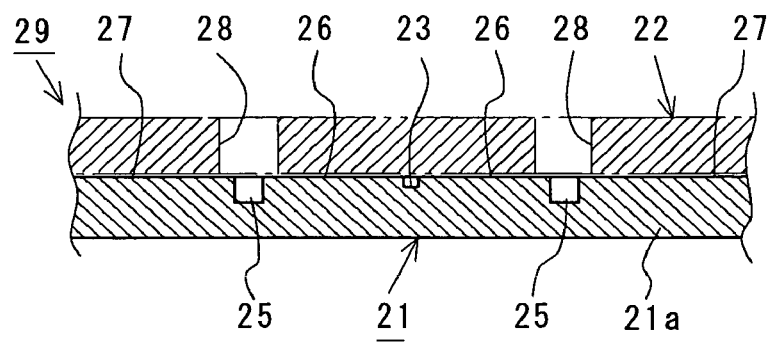
FIG. 16 is a sectional view taken along line XVI-XVI of FIG. 15.

FIGS. 15 and 16 show a first modified example of the second preferred embodiment of a plate assembly according to the present invention.

In this example, the construction of the plate assembly is the same as that in the first preferred embodiment, except that the positions of the adhesive injecting holes 28 are different from those in the first preferred embodiment. That is, in this example, the adhesive injecting holes 28 are open to the bonded surface 26, pass partition groove 25 and butt surface 27 of the plate member 21.

According to this example with such a construction, if the adhesive is dropped from the adhesive injecting holes 28, the adhesive dropped onto the bonded surface 26 permeates the fine gap 34 between the bonded surface 26 of the plate member 21 and the lid member 22 due to capillarity, and excessive part of the adhesive flows into the pass partition groove 25, or the adhesive dropped into the pass partition groove 25 permeates the fine gap 34 between the bonded surface 26 of the plate member 21 and the lid member 22 due to capillarity (see FIG. 14A). Therefore, this example can obtain the same advantageous effects as those in the above described second preferred embodiment.

Figure 17:
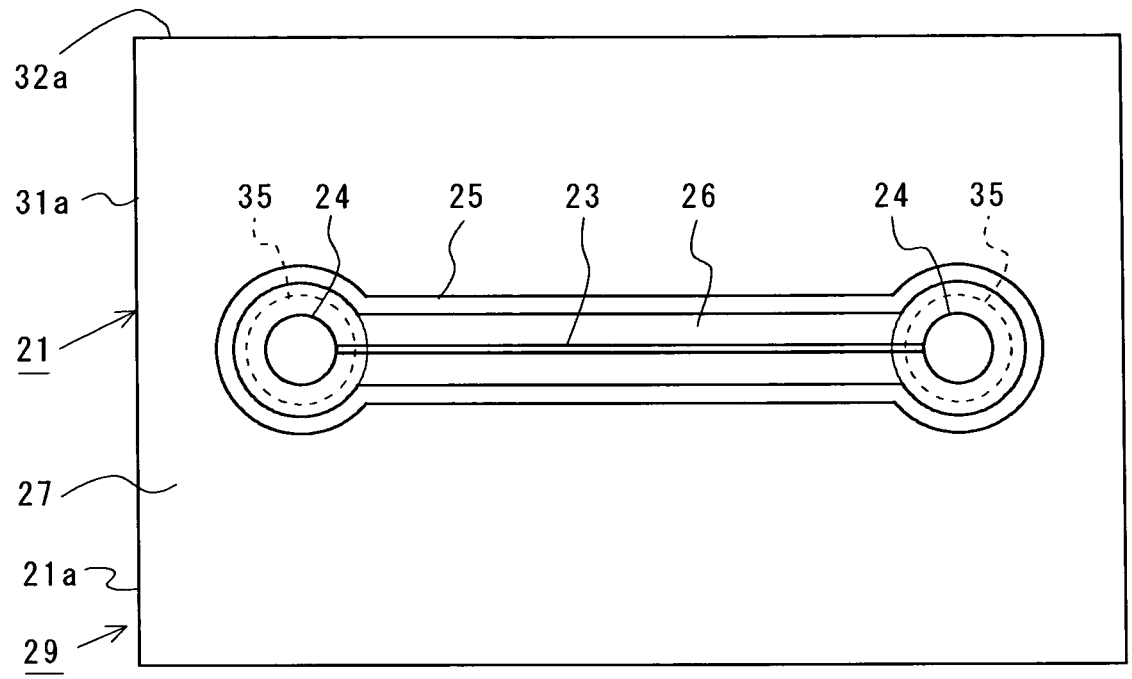
FIG. 17 is a plan view of a second modified example of a plate member in the second preferred embodiment of a plate assembly according to the present invention.
Figure 18:
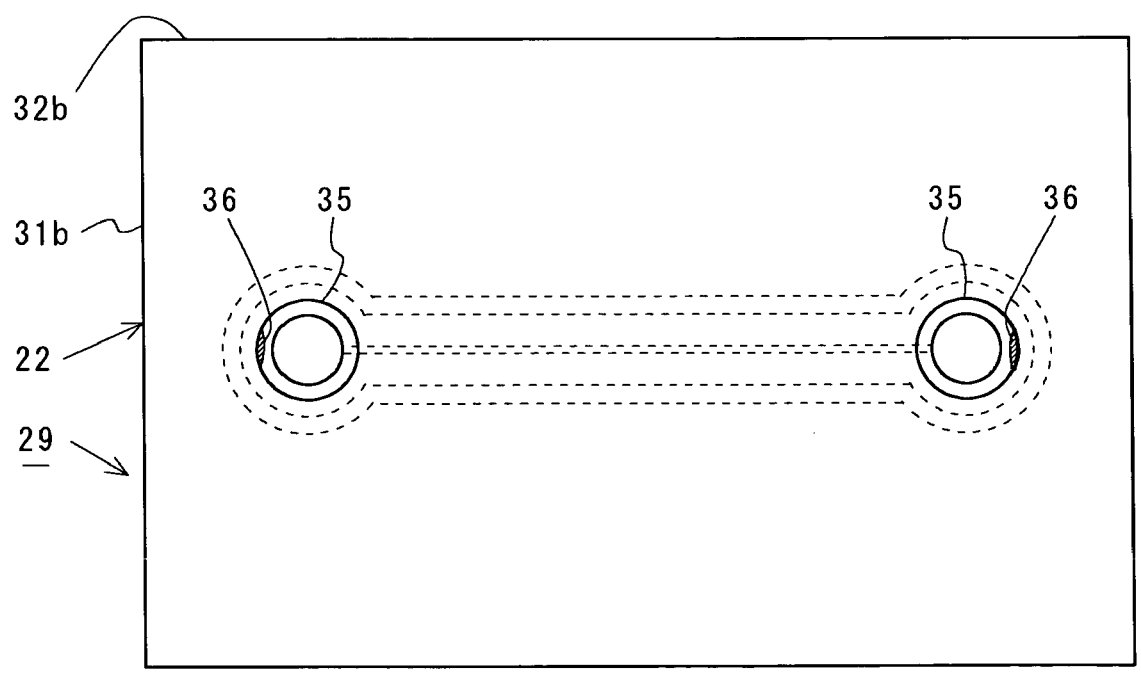
FIG. 18 is a plan view of a lid member bonded to a plate member of the plate assembly of FIG. 17.

FIGS. 17 and 18 show a second modified example of the second preferred embodiment of a plate assembly according to the present invention.

In this example, the through holes 35 of the lid member 22 open to both end portions of the fine groove 23 are also used as adhesive injecting holes. In this example, when the adhesive is dropped from the through holes 35, target dropped regions are preferably regions (regions 36 shown by slant lines in FIG. 18) which are positioned above the bonded surface 26 on the opposite side to the fine groove 23 and which extend along the walls of the through holes 35. If the adhesive is dropped in such regions, the dropped adhesive permeates the fine gap 34 between the bonded surface 26 and the lid member 22 due to capillarity, so that it is possible to prevent the adhesive from entering the fine groove 23 (see FIG. 14A). Furthermore, the through holes 35 of the lid member 22 have such a size as to be capable of ensuring the sufficiently large bonded surface 26 around the sample receiving holes 24, and have a greater diameter than that of the sample receiving holes 24.

Third Preferred Embodiment

Figure 19:
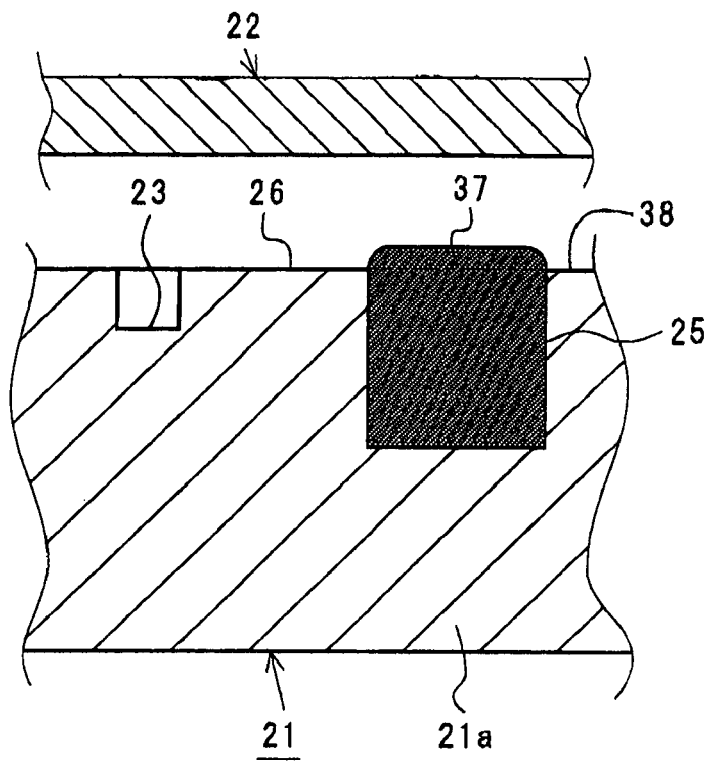
FIG. 19 is a sectional view of a bonded structure in the third preferred embodiment of a plate assembly according to the present invention before a lid member is bonded to a plate member.
Figure 20:
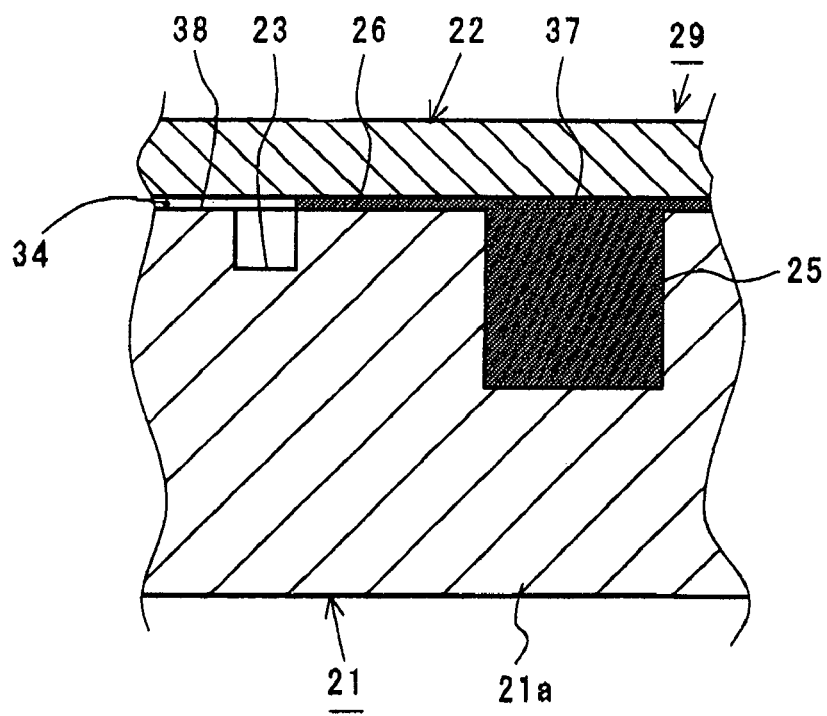
FIG. 20 is a sectional view of a bonded structure in the third preferred embodiment of a plate assembly according to the present invention when the lid member is bonded to the plate member.

FIGS. 19 and 20 show the third preferred embodiment of a plate assembly according to the present invention. In this preferred embodiment, a sufficient amount of adhesive 37 is previously injected into the pass partition groove 25 of the plate member 21 to be pulled from the pass partition groove 25 by surface tension. Then, if the lid member 22 is aligned with and arranged on the top face 38 of the plate member 21, the adhesive 37 instantaneously permeates the fine gap 34 between the bonded surface 26 of the plate member 21 and the lid member 22 due to capillarity. In this preferred embodiment similar to the above described preferred embodiments, capillarity is not caused between the lid member 22 and the fine groove 23 of the plate member 21, so that the adhesive 37 does not enter the fine groove 23.

Fourth Preferred Embodiment

Figure 21:
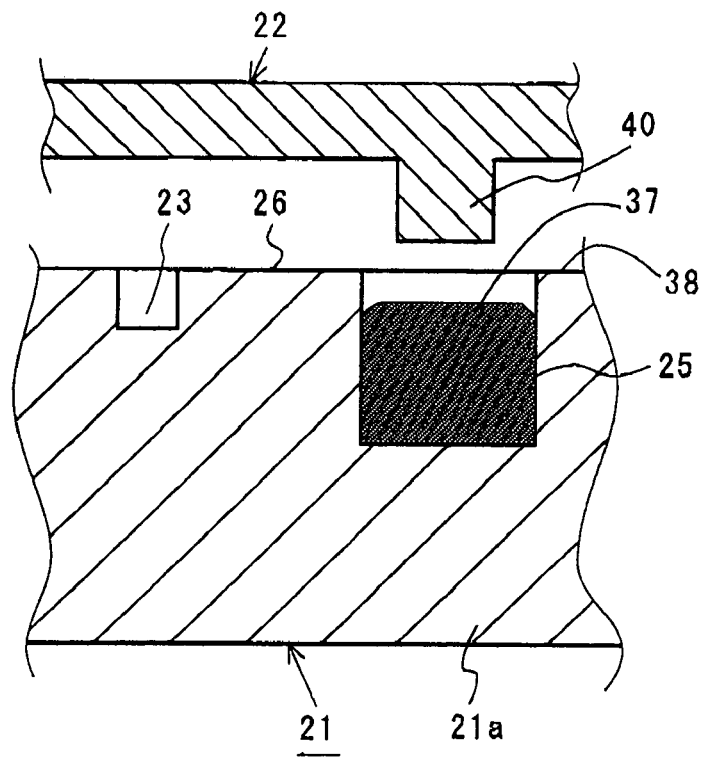
FIG. 21 is a sectional view of a bonded structure in the fourth preferred embodiment of a plate assembly according to the present invention before a lid member is bonded to a plate member.
Figure 22:
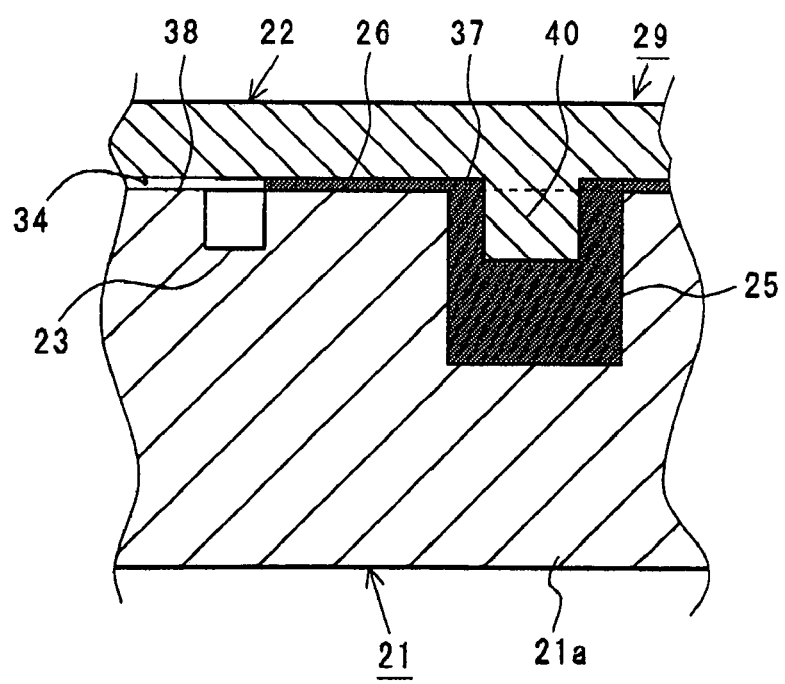
FIG. 22 is a sectional view of a bonded structure in the fourth preferred embodiment of a plate assembly according to the present invention when the lid member is bonded to the plate member.

FIGS. 21 and 22 show the fourth preferred embodiment of a plate assembly according to the present invention. In this preferred embodiment, the pass partition groove 25 of the plate member 21 is filled with such an amount of adhesive 37 that the adhesive rises from the bonded surface 26 by surface tension when a protrusion 40, which will be described later, is inserted into the pass partition groove 25. On the other hand, when the lid member 22 is aligned with and arranged on the top face 38 of the plate member 21, the protrusion 40 is precisely fitted into the fine groove 23 of the plate member 21 to serve as a means for positioning the lid member 22 to the plate member 21, so that the lid member 22 and the plate member 21 are positioned.

With this construction, if the adhesive 37 pushed out from the pass partition groove 37 by the protrusion 40 is pushed into the fine groove 34 between the lid member 22 and the bonded surface 26, the adhesive 37 permeates the fine groove 34 between the lid member 22 and the plate member 21 due to capillarity. Thus, it is possible to expect the same advantageous effects as those in the above described third preferred embodiment.

Fifth Preferred Embodiment

FIGS. 23 through 26C show the fifth preferred embodiment of a plate assembly according to the present invention. In this preferred embodiment, a plurality of spacer protrusions 51 are formed at appropriate intervals on at least one of the bonded surface 4 of the plate member 1 and the face (bottom face) 11 of the lid member 2 facing the bonded surface 4.

Figure 23:
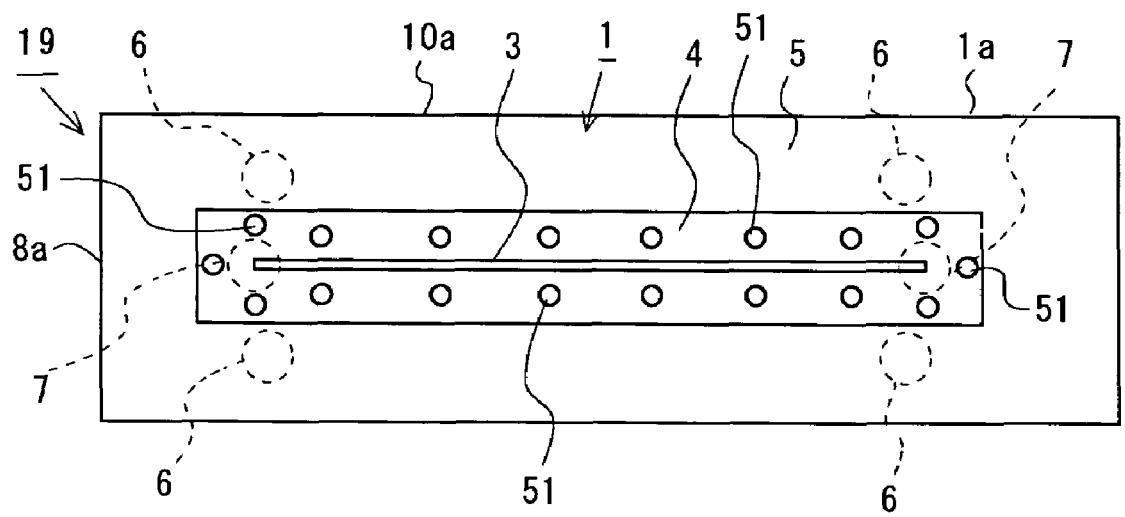
FIG. 23 is a plan view of a plate member in the fifth preferred embodiment of a plate assembly according to the present invention.
Figure 25:
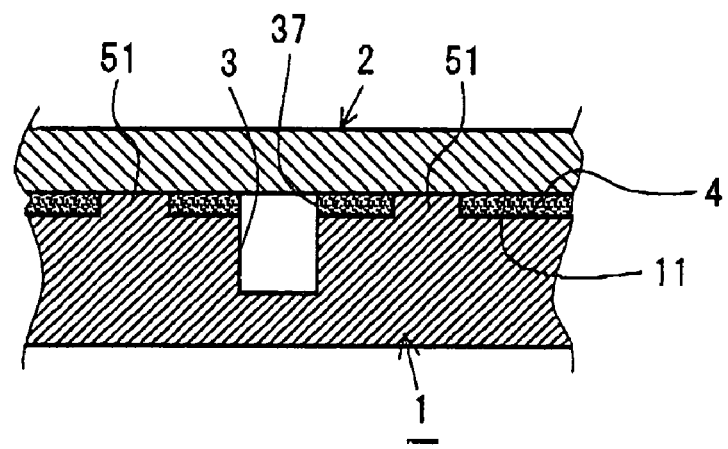
FIG. 25 is a sectional view of a bonded structure in the fifth preferred embodiment of a plate assembly according to the present invention, which is taken along a line perpendicular to a fine groove.

For example, FIG. 23 shows the plurality of spacer protrusions 51 formed at appropriate intervals on the bonded surface 4 of the plate member 1. FIG. 25 shows the lid member 2 aligned with and bonded to the plate member 1 having the spacer protrusions 51. As shown in FIG. 25, if the spacer protrusions 51 formed on the bonded surface 4 of the plate member 1 contact the facing lid member 2, a gap is formed between the bonded surface 4 of the plate member 1 and the lid member 2 so that an adhesive 37 can permeate the gap due to capillarity. That is, the spacer protrusions 51 formed on the bonded surface 4 of the plate member 1 have such a height that the adhesive 37 can permeate the gap between the bonded surface 4 of the plate member 1 and the lid member 2 due to capillarity.

Figure 26A:
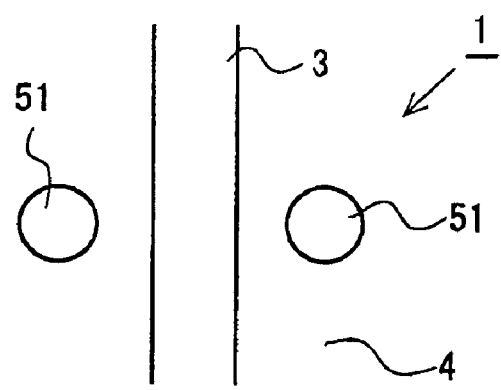
FIG. 26A is a plan view showing the relationship between spacer protrusions and a fine groove in the fifth preferred embodiment of a plate assembly according to the present invention.
Figure 26B:
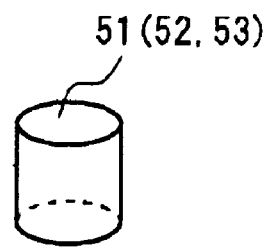
FIG. 26B is a perspective view of an example of a spacer protrusion in the fifth preferred embodiment of a plate assembly according to the present invention.
Figure 26C:
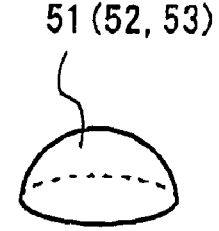
FIG. 26C is a perspective view of another example of a spacer protrusion in the fifth preferred embodiment of a plate assembly according to the present invention.

FIG. 26A shows the relationship between the fine groove 3 and spacer protrusions 51 formed on the bonded surface 4 of the plate member 1, and FIGS. 26B and 26C show the shape of one of the spacer protrusions 51 formed on the bonded surface 4 of the plate member 1. For production, the spacer protrusion 51 is preferably cylindrical as shown in FIG. 26B or substantially hemispherical as shown in FIG. 26C. The shape of the spacer protrusion 51 should not be limited thereto, but it may be a truncated cone or another space.

Figure 24:
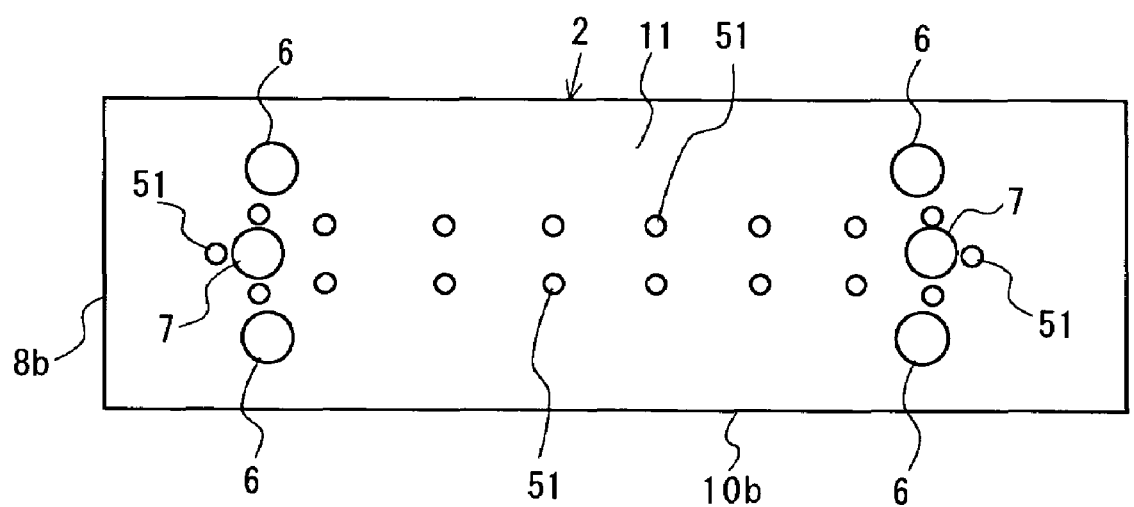
FIG. 24 is a bottom view of a lid member in the fifth preferred embodiment of a plate assembly according to the present invention.

FIG. 24 shows an embodiment wherein a plurality of spacer protrusions 51 shown in FIG. 26B or 26C are formed at appropriate intervals on the bottom face 11 of the lid member 2 bonded to the plate member 1. Alternatively, the spacer protrusions 51 may be formed on the bonded surface 4 of the plate member 1 as shown in FIG. 23, and the spacer protrusions 51 may be formed on the bottom face 11 of the lid member 2 bonded to the plate member 1, so that the spacer protrusions 51 may butt the facing member to form such a gap between the bonded surface 4 of the plate member 1 and the lid member 2 that the adhesive 37 can permeate the gap due to capillarity.

Figure 27:
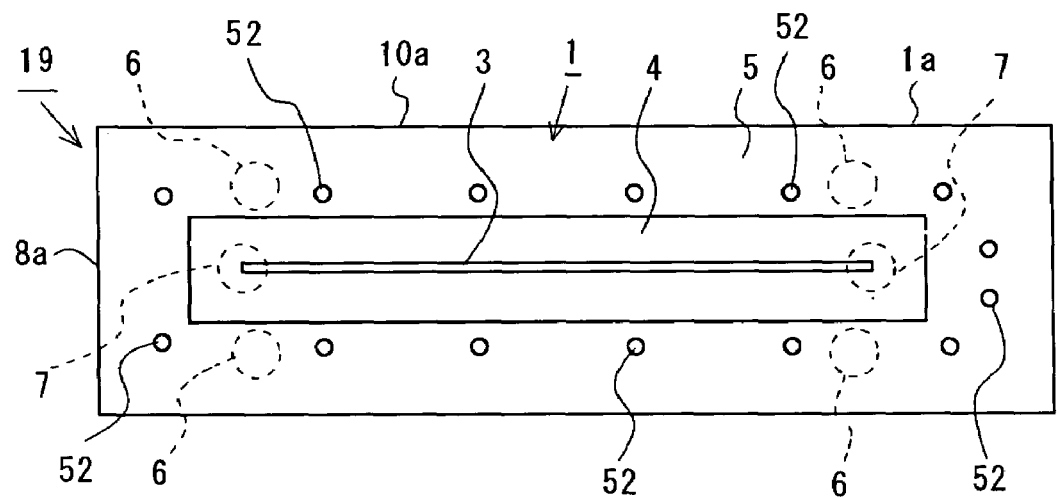
FIG. 27 is a plan view of a first modified example of a plate member in the fifth preferred embodiment of a plate assembly according to the present invention.
Figure 28:
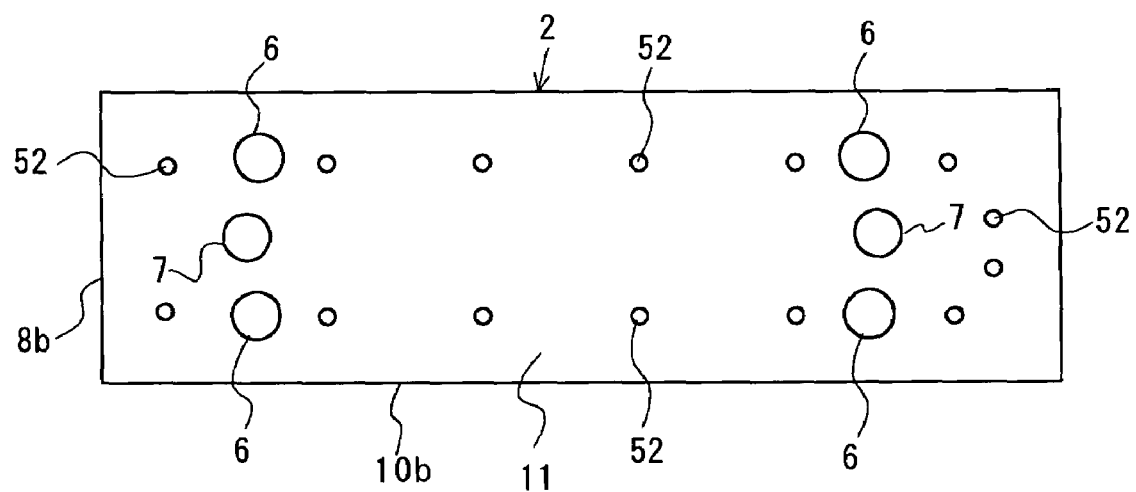
FIG. 28 is a bottom view of a first modified example of a lid member in the fifth preferred embodiment of a plate assembly according to the present invention.

FIGS. 27 and 28 show a first modified example of the fifth preferred embodiment of a plate assembly according to the present invention. In this example, as shown in FIG. 27, a plurality of spacer protrusions 52 are formed at appropriate intervals on the adhesive relief portion 5 of the plate member 1 so as to surround the bonded surface 4. As described in the first preferred embodiment, the adhesive relief portion 5 of the plate member 1 is recessed around the adhesive surface 4. Therefore, the height of the spacer protrusions 52 formed on the adhesive relief portion 5 of the plate member 1 is greater than that of the spacer protrusion 51 by the depth of the adhesive relief portion 5 recessed from the adhesive surface 4. As a result, if the lid member 2 is arranged on the plate member 1 so that the spacer protrusions 52 formed on the adhesive relief 5 of the plate member 1 butt the lid member 2, a gap is formed between the bonded surface 4 of the plate member 1 and the lid member 2 so that the adhesive can permeate the gap due to capillarity.

Alternatively, as shown in FIG. 28, the plurality of spacer protrusions 52 may be formed at appropriate intervals on the face 11 of the lid member 2 facing the adhesive relief portion 5 of the plate member 1. In this case, similar to the case shown in FIG. 27, the height of the spacer protrusions 52 is greater than that of the spacer protrusion 51 by the depth of the adhesive relief portion 5 recessed from the adhesive surface 4. As a result, if the lid member 2 is aligned with and arranged on the plate member 1 so that the spacer protrusions 52 formed on the lid member 2 butt the adhesive relief portion 5 of the plate member 1, a gap is formed between the bonded surface 4 of the plate member 1 and the lid member 2 so that the adhesive can permeate the gap due to capillarity. Furthermore, the spacer protrusions 52 may be formed on both of the adhesive relief portion 5 of the plate member 1 and the lid member 2.

Figure 29:
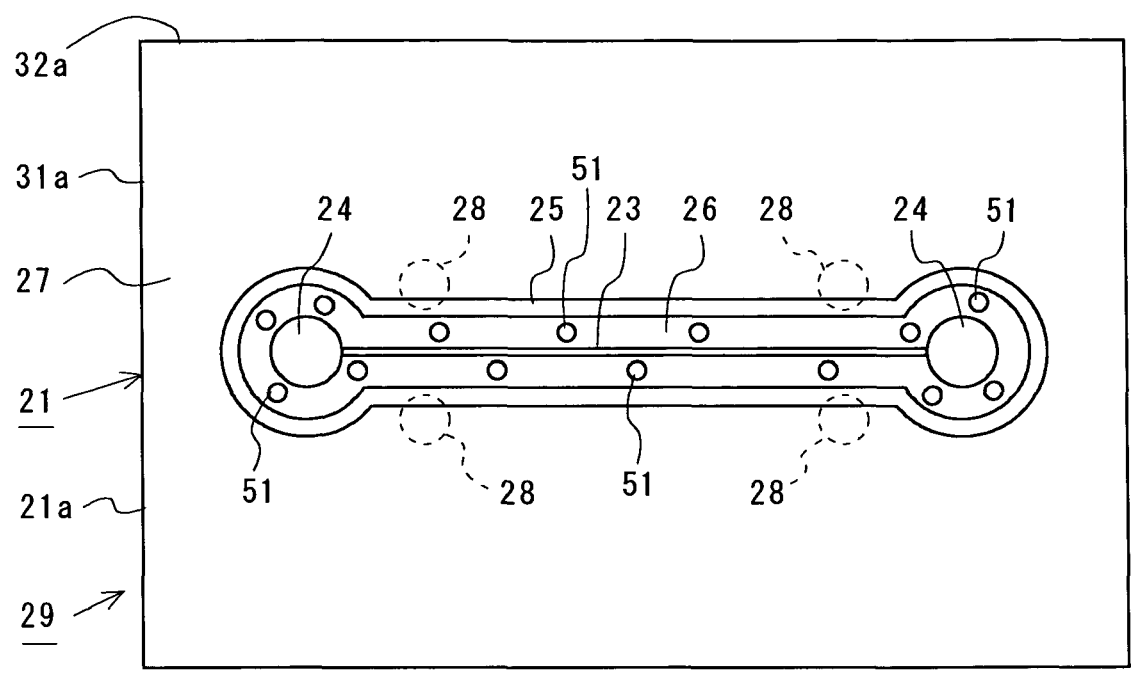
FIG. 29 is a plan view of a second modified example of a plate member in the fifth preferred embodiment of a plate assembly according to the present invention.
Figure 30:
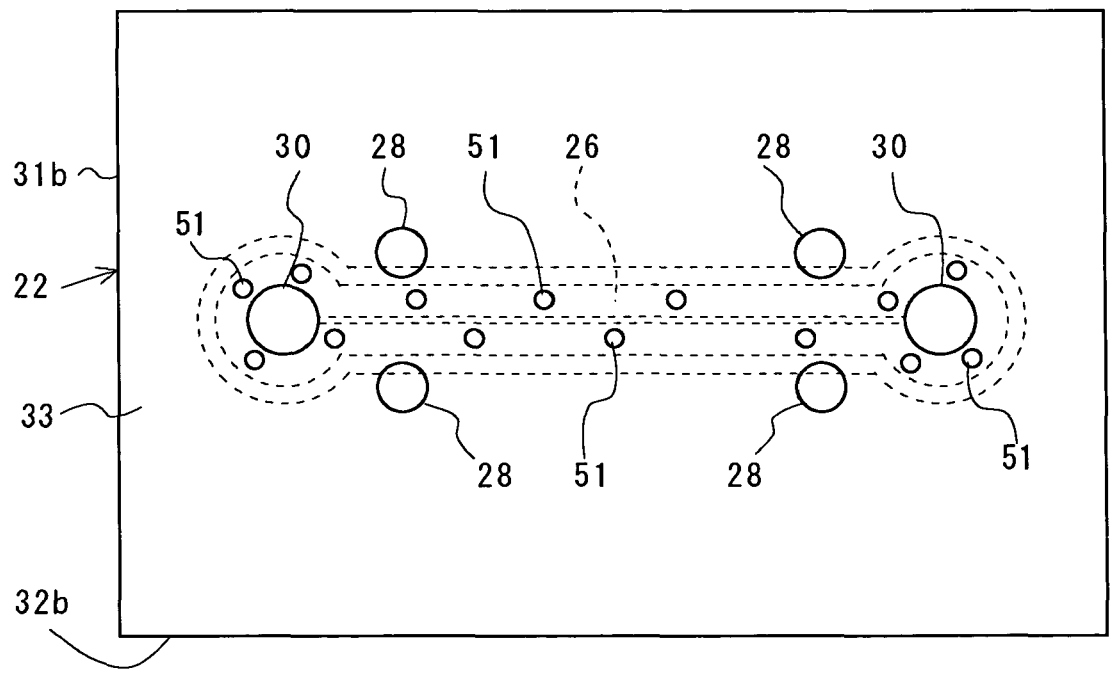
FIG. 30 is a bottom view of a second modified example of a lid member in the fifth preferred embodiment of a plate assembly according to the present invention.

FIGS. 29 and 30 show a second modified example of the fifth preferred embodiment of a plate assembly according to the present invention. In this example, spacer protrusions 51 are formed on at least one of the bonded surface 26 of the plate member 21 and the lid member 22 in the second preferred embodiment.

FIG. 29 shows an example where a plurality of spacer protrusions 51 are formed on the bonded surface 26 of the plate member 21 at appropriate intervals. If the lid member 22 is aligned with and arranged on the plate member 21 so that the spacer protrusions 51 of the plate member 21 butt the lid member 22, a gap is formed between the bonded surface 26 of the plate member 21 and the lid member 22 so that the adhesive can permeate the gap due to capillarity.

FIG. 30 shows an example where a plurality of spacer protrusions 51 are formed at appropriate intervals on the bottom face 33 of the lid member 22 facing the bonded surface 26 of the plate member 21. If the lid member 22 is aligned with and arranged on the plate member 21 so that the spacer protrusions 51 of the lid member 22 butt the bonded surface 26 of the plate member 21, a gap is formed between the bonded surface 26 of the plate member 21 and the lid member 22 so that the adhesive can permeate the gap due to capillarity. Furthermore, the spacer protrusions 51 may be formed on both of the bonded surface 26 of the plate member 21 and the lid member 22.

Figure 31:
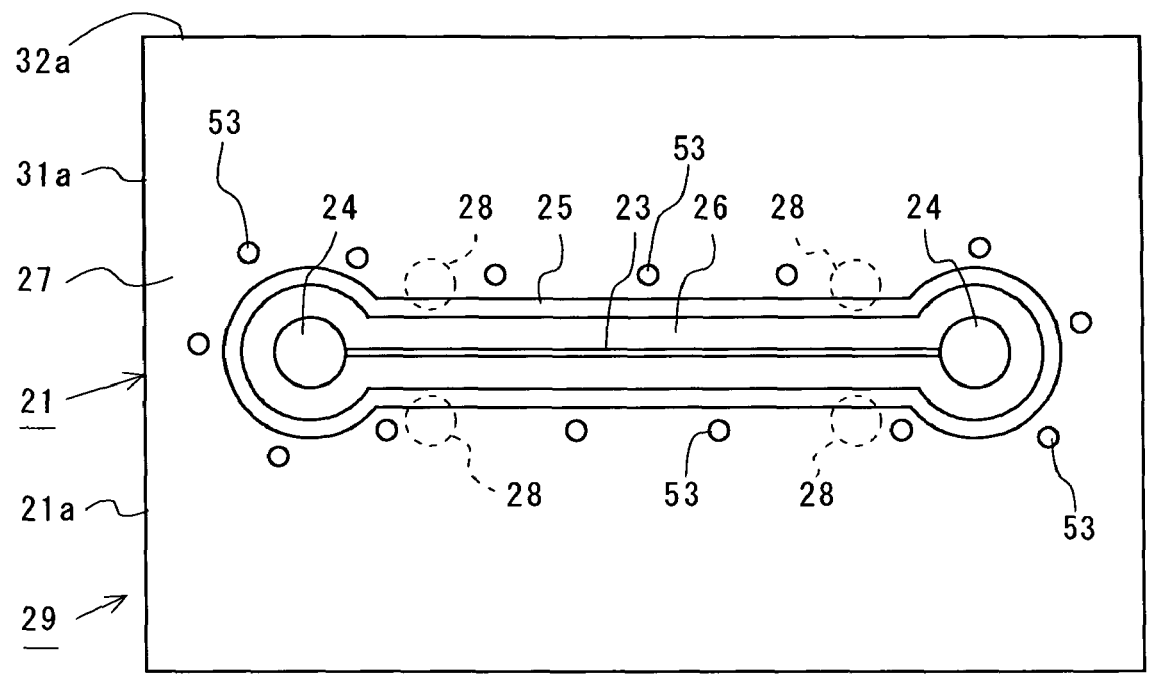
FIG. 31 is a plan view of a third modified example of a plate member in the fifth preferred embodiment of a plate assembly according to the present invention.
Figure 32:
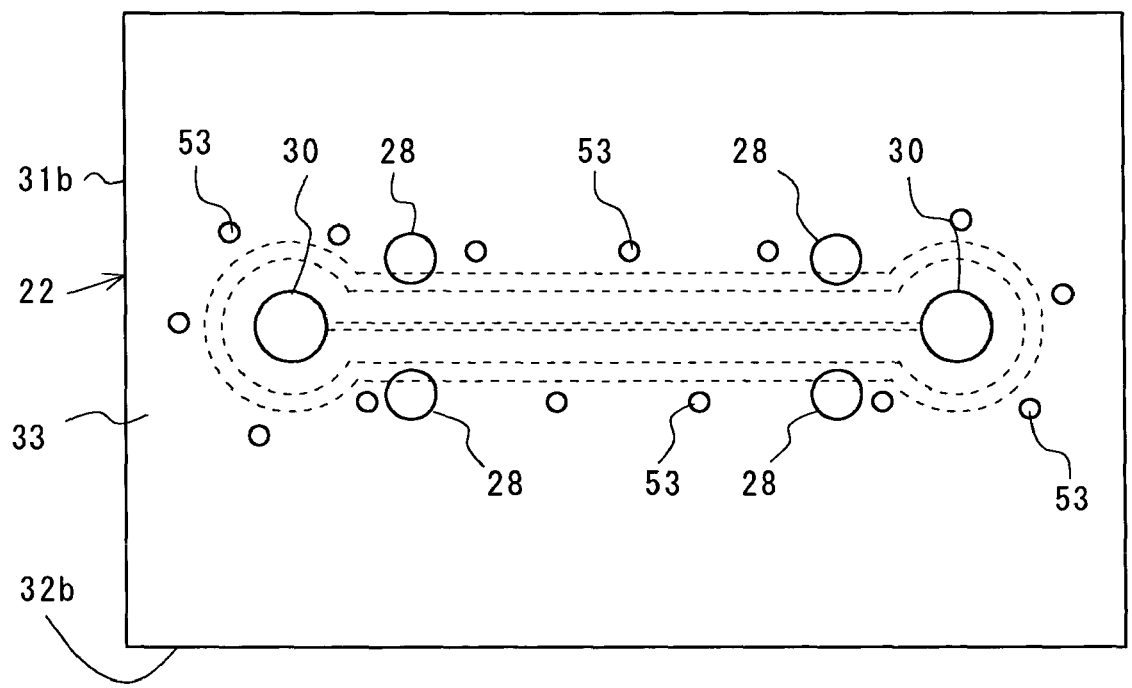
FIG. 32 is a bottom view of a third modified example of a lid member in the fifth preferred embodiment of a plate assembly according to the present invention.

FIGS. 31 and 32 show a third modified example of the fifth preferred embodiment of a plate assembly according to the present invention. In this example, spacer protrusions 53 are formed on at least one of the butt surface 27 of the plate member 21 and the lid member 22 in the second preferred embodiment.

FIG. 31 shows an example where a plurality of spacer protrusions 53 are formed on the butt surface 27 of the plate member 21 at appropriate intervals. If the lid member 22 is aligned with and arranged on the plate member 21 so that the spacer protrusions 53 of the plate member 21 butt the lid member 22, a gap is formed between the bonded surface 26 of the plate member 21 and the lid member 22 so that the adhesive can permeate the gap due to capillarity.

FIG. 32 shows an example where a plurality of spacer protrusions 53 are formed at appropriate intervals on the bottom face 33 of the lid member 22 facing the butt surface 27 of the plate member 21. If the lid member 22 is aligned with and arranged on the plate member 21 so that the spacer protrusions 53 of the lid member 22 butt the butt surface 27 of the plate member 21, a gap is formed between the bonded surface 26 of the plate member 21 and the lid member 22 so that the adhesive can permeate the gap due to capillarity. Furthermore, the spacer protrusions 53 may be formed on both of the butt surface 27 of the plate member 21 and the facing bottom face 33 of the lid member 22.

According to this preferred embodiment with such a construction, the spacer protrusions 51, 52 or 53 formed on at least one of the plate member 1 or 21 and the lid member 2 or 22 can form a gap between the bonded surface 4 or 26 of the plate member 1 or 21 and the lid member 2 or 22 so that the adhesive can permeate the gap due to capillarity. Therefore, even if the plate member 1, 21 and/or the lid member 2, 22 is deformed by warpage or the like, the plate member 1 or 21 and the lid member 2 or 22 can be aligned with each other to be held so as to rectify the deformation, such as warpage, so that it is possible to allow the adhesive to permeate the gap between the bonded surface 4 or 26 of the plate member 1 or 21 and the lid member 2 or 22 due to capillarity and it is possible to surely bond and fix the lid member 2 or 22 to the plate member 1 or 21.

Sixth Preferred Embodiment

Figure 33:
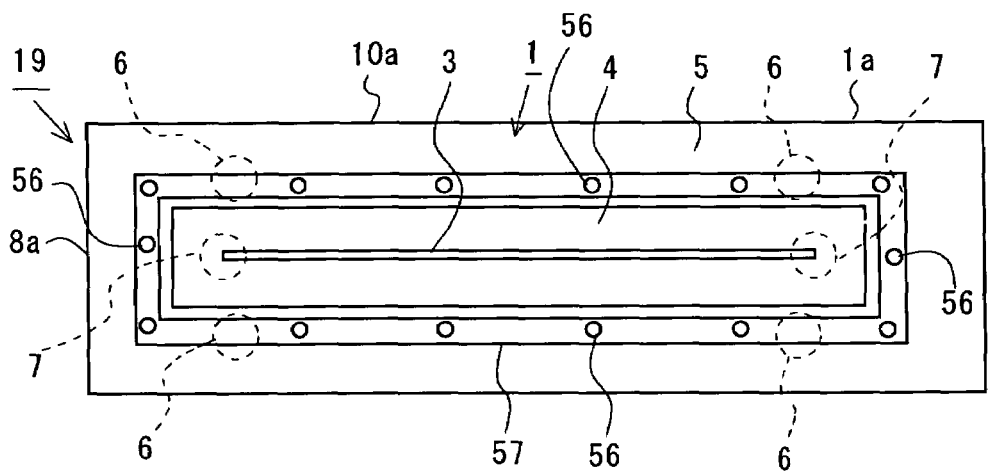
FIG. 33 is a plan view of a plate member in the sixth preferred embodiment of a plate assembly according to the present invention.

FIG. 33 shows the sixth preferred embodiment of a plate assembly according to the present invention. In this preferred embodiment, spacers 56 are provided between the plate member 1 and the lid member 2 in the first preferred embodiment.

In FIG. 33, a spacer housing groove 57 is formed in the adhesive relief portion 5 of the plate member 1 so as to surround the bonded surface 4. The spacer housing groove 57 houses therein a plurality of spherical or cylindrical spacers 56. If a lid member (not shown) is aligned with and arranged on the plate member 1 housing therein the spacers 56, a gap is formed between the bonded surface 4 of the plate member 1 and the lid member so that an adhesive can permeate the gap due to capillarity.

Figure 34:
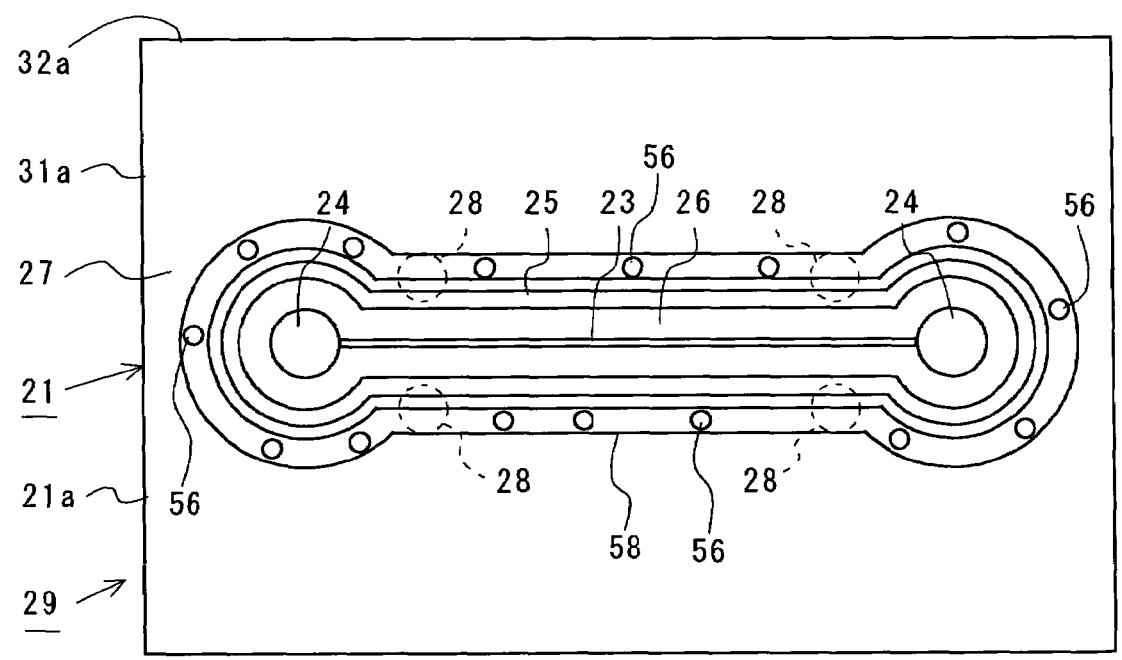
FIG. 34 is a plan view of a modified example of a plate member in the sixth preferred embodiment of a plate assembly according to the present invention.

FIG. 34 shows a modified example of the sixth preferred embodiment of a plate assembly according to the present invention. In this example, spacers 56 are provided between the plate member 21 and the lid member 22 in the second preferred embodiment.

In FIG. 34, a spacer housing groove 58 is formed in the butt surface 27 of the plate member 21 so as to surround the bonded surface 26. The spacer housing groove 58 houses therein a plurality of spherical or cylindrical spacers 56. If a lid member (not shown) is aligned with and arranged on the plate member 21 housing therein the spacers 56, a gap is formed between the bonded surface 26 of the plate member 21 and the lid member so that an adhesive can permeate the gap due to capillarity.

In this preferred embodiment, the spacers 56 housed between the plate member 1 or 21 and the lid member can form the gap between the bonded surface 4 or 26 of the plate member 1 or 21 and the lid member so that the adhesive can permeate the gap due to capillarity. Therefore, even if the plate member 1 or 21 and/or the lid member is deformed by warpage or the like, the plate member 1 or 21 and the lid member can be aligned with each other to be held so as to rectify the deformation, such as warpage, so that it is possible to allow the adhesive to permeate the gap between the bonded surface 4 or 26 of the plate member 1 or 21 and the lid member due to capillarity and it is possible to surely bond and fix the lid member to the plate member 1 or 21.

According to this preferred embodiment, the spacers 56 are housed in the spacer housing groove 57 or 58. Thus, the spacers 56 do not enter the fine groove 3 or 23 by mistake, and the spacers 56 do not fill up the fine groove 3 or 23. In addition, there is not some possibility that the spacers 56 fall away from the plate member 1 or 21.

While the spacer housing groove 57 or 58 has been formed in the plate member 1 or 21 in FIG. 33 or 34, the spacer housing groove 57 or 58 may be formed in the lid member 2 or 22, or in both of the plate member 1 or 21 and the lid member 2 or 22 to house therein a plurality of spacers 56 between the plate member 1 or 21 and the lid member 2 or 22 to form a gap between the bonded surface 4 or 26 of the plate member 1 or 21 and the lid member 2 or 22 so that an adhesive can permeate the gap due to capillarity. Alternatively, the spacer housing groove 57 or 58 may be formed in the bonded surface 4 or 26 to house therein a plurality of spacers 56. In FIG. 34, the spacer groove 58 may be omitted so that the spacers 56 are housed in the pass partition groove 25. That is, the spacers 56 may be housed in the pass partition groove 25 shown in FIG. 11.

While the spacer housing groove 57 or 58 has surrounded the whole circumference of the fine groove 3 or 23 in this preferred embodiment, the present invention should not be limited thereto, but a plurality of grooves having a predetermined length may be provided. Alternatively, recessed portions suitable for the shape of the spacers 56 may be formed so as to correspond to the arrangement of the spacers 56.

Seventh Preferred Embodiment

FIGS. 35A through 35D show examples of the seventh preferred embodiment of a plate assembly according to the present invention, wherein the strength of adhesive bonding between the lid member 2 and the plate member 1 is enhanced.

Figure 35A:
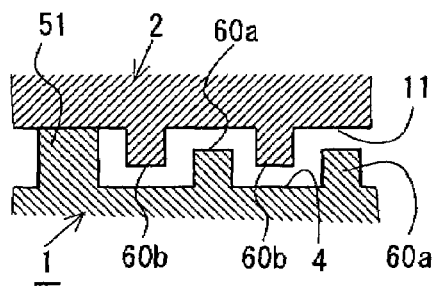
FIG. 35A is a sectional view of a first example of a bonded structure in the seventh preferred embodiment of a plate assembly according to the present invention.

FIG. 35A shows an example where protrusions 60a and 60b having a lower height than that of the spacer protrusions 51 are formed on the bonded surface 4 of the plate member 1 and the facing bottom face 11 of the lid member 2, respectively, to align and arrange the lid member 2 with and on the plate member 1 so as to insert the protrusion 60b of the lid member 2 into a space between the spacer protrusion 51 and protrusion 60a of the plate member 1 or between the protrusions 60a and 60a of the plate member 1. In this example, a gap allowing the permeation of an adhesive is formed between the spacer protrusion 51 and the protrusion 60b or between the protrusions 60a and 60b, and the surface area of the adhesive contacting the plate member 1 and lid member 2 is greater than that in the above described fifth preferred embodiment of a plate assembly according to the present invention, so that the bonded area increases to increase the strength of adhesive bonding between the lid member 2 and the plate member 1.

Figure 35B:
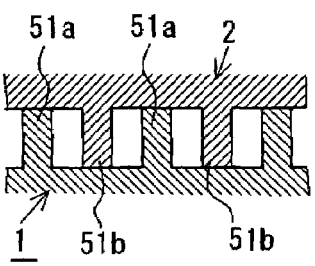
FIG. 35B is a sectional view of a second example of a bonded structure in the seventh preferred embodiment of a plate assembly according to the present invention.

FIG. 35B shows an example where the lid member 2 is aligned with and arranged on the plate member 1 so as to insert the protrusions 51b of the lid member 2 into spaces between the spacer protrusions 51a and 51a of the plate member 1. According this example, a gap is formed between the adjacent spacer protrusions 51a and 51b so that an adhesive can permeate the gap due to capillarity, and the bonded area can be increased to increase the strength of adhesive bonding between the plate member 1 and the lid member 2.

Figure 35C:
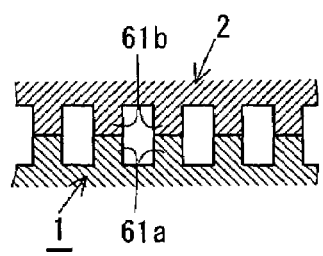
FIG. 35C is a sectional view of a third example of a bonded structure in the seventh preferred embodiment of a plate assembly according to the present invention.

FIG. 35C shows an example where the lid member 2 is aligned with and arranged on the plate member 1 so that protrusions 61a formed between spacer protrusions (not shown) on the plate member 1 butt protrusions 61b formed on the lid member 2. According to this example, a gap is formed between the adjacent protrusions 61a and 61b so that an adhesive can permeate the gap due to capillarity, thereby increasing the bonded area to increase the strength of adhesive bonding between the lid member 2 and the plate member 1. Furthermore, the protrusions 61a and 61b shown in this figure may be spacer protrusions.

Figure 35D:
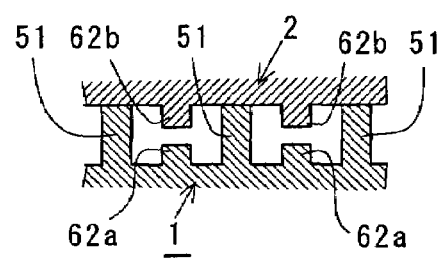
FIG. 35D is a sectional view of a fourth example of a bonded structure in the seventh preferred embodiment of a plate assembly according to the present invention.

FIG. 35D shows an example where protrusions 62a being half or less than the height of the spacer protrusions 51 are formed between the spacer protrusions 51 and 51 of the plate member 1 and wherein 62b being substantially the same as the protrusions 62a are formed on the lid member 2. According to this example, the protrusions 62a and 62b are arranged in spaces between the spacer protrusions 51 and 51, so that the bonded area increases to increase the strength of adhesive bonding between the lid member 2 and the plate member 1.

Eighth Preferred Embodiment

Figure 36A:
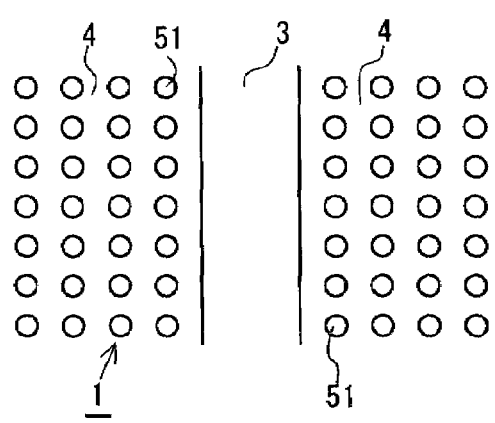
FIG. 36A is an enlarged plan view of an example of a part of the eighth preferred embodiment of a plate assembly according to the present invention, wherein spacer protrusions are arranged at substantially regular intervals.
Figure 36B:
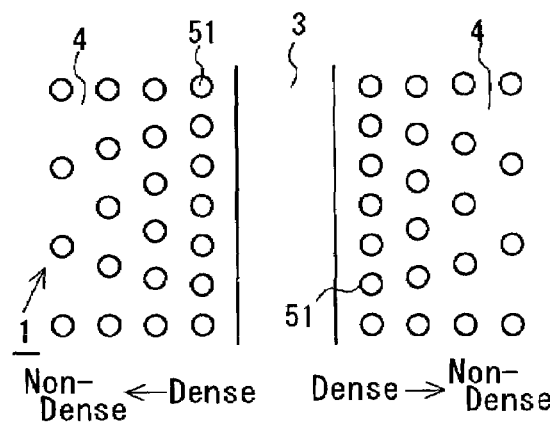
FIG. 36B is an enlarged plan view of another example of a part of the eighth preferred embodiment of a plate assembly according to the present invention, wherein the density of spacer protrusions varies.

FIGS. 36A and 36B show examples of arrangement of spacer protrusions 51 in the eighth preferred embodiment of a plate assembly according to the present invention.

FIG. 36A shows an example where a plurality of spacer protrusions 51 are formed on the bonded surface 4 at substantially regular intervals. FIG. 36B shows an example where the intervals of the spacer protrusions 51 formed on the bonded surface 4 vary from dense to non-dense as a distance from the fine groove 3 increases. According to the example shown in FIG. 36B, the flow resistance of an adhesive is lower on the far side from the fine groove 3, and the flow resistance of the adhesive is higher in the vicinity of the fine groove 3. As a result, according to the example shown in FIG. 36B, it is possible to more effectively prevent the adhesive from flowing into the fine groove 3.

As shown in FIGS. 36A and 36B, the nearest spacer protrusions 51 to the fine groove 3 are formed so as to be spaced from the fine groove 3 by a predetermined distance. With this construction, it is possible to prevent the adhesive, which permeates the gap between the bonded surface of the plate member and the lid member due to capillarity, from protruding toward the fine groove 3.

Furthermore, the sectional shape of the fine groove 3 or 23 should not be limited to that in the above described preferred embodiments, but the fine groove 3 or 23 may have another shape, such as semicircle, U-shape, or substantially triangle.

In addition, the sectional shape of the pass partition groove 25 should not be limited to that in the above described preferred embodiments, but the pass partition groove 25 may have another shape, such as semicircle, U-shape, or substantially triangle.

While the sectional shape of the protrusion 40 has been rectangular in the fourth preferred embodiment, the present invention should not be limited thereto, but it may be a suitable shape, such as triangle or semicircle. In addition, the protrusion 40 may be formed so as to be fitted into the whole circumferential portion of the pass partition groove 25, or protrusions 40 may be formed at regular intervals so as to be partially fitted into the pass partition groove 25.

The plane shape of the fine groove 3 or 23 in the above described preferred embodiments should not be limited to be linear (see FIGS. 1 and 11), but the present invention may be applied to a plate assembly having a fine groove having cross, Y-shape, curve or another complicated shape. Of course, the present invention can be applied to a plate assembly having a fine groove having a constant width and depth, but the invention may be applied to a plate assembly having a fine groove, the width and depth of which vary.

While the capillary electrophoresis chips 19 and 29 used for carrying out tests in the field of biochemistry have been described as examples for convenience of explanation in the above described preferred embodiments, the present invention should not be limited thereto, but the invention may be widely applied to a plate assembly which has a recessed portion for carrying out chemical tests in various fields other than the field of biochemistry, such as the fields of synthetic chemistry, physical chemistry and analytical chemistry.

As described above, according to the present invention, the adhesive is designed to permeate the fine gap between the plate member and the lid member due to capillarity, so that the lid member can be simply bonded and fixed to the plate member without allowing the adhesive to enter the fine groove.

According to the present invention, the adhesive relief portion is formed outside of the bonded surface, so that the amount of the adhesive to be used can be saved.

According to the present invention, the spacer protrusions formed on at least one of the plate member and the lid member can form the gap between the bonded surface of the plate member and the lid member so that the adhesive can permeate the gap due to capillarity. Therefore, even if the plate member and/or the lid member is deformed by warpage or the like, the plate member and the lid member can be aligned with each other to be held so as to rectify the deformation, such as warpage, so that it is possible to allow the adhesive to permeate the gap between the bonded surface of the plate member and the lid member due to capillarity and it is possible to surely bond and fix the lid member to the plate member.

According to the present invention, the spacers are provided between the plate member and the lid member to form the gap between the bonded surface of the plate member and the lid member so that the adhesive can permeate the gap due to capillarity. Therefore, even if the plate member and/or the lid member is deformed by warpage or the like, the plate member and the lid member can be aligned with each other to be held so as to rectify the deformation, such as warpage, so that it is possible to allow the adhesive to permeate the gap between the bonded surface of the plate member and the lid member due to capillarity and it is possible to surely bond and fix the lid member to the plate member.

Ninth Preferred Embodiment

Figure 37:
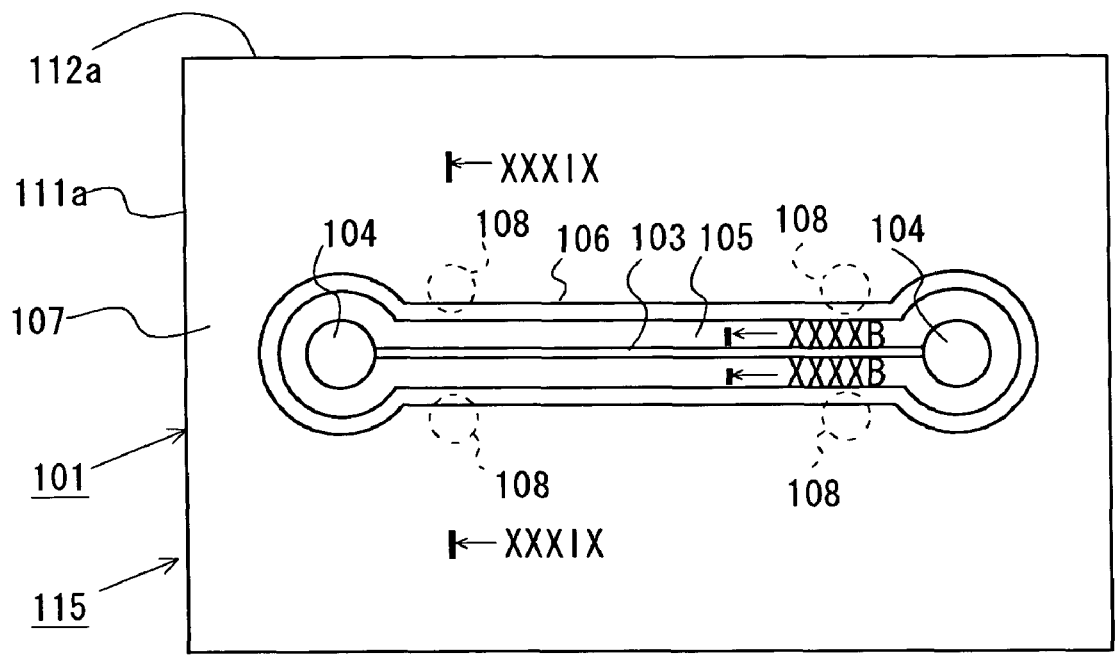
FIG. 37 is a plan view of a plate member in the ninth preferred embodiment of a plate assembly according to the present invention.
Figure 38:
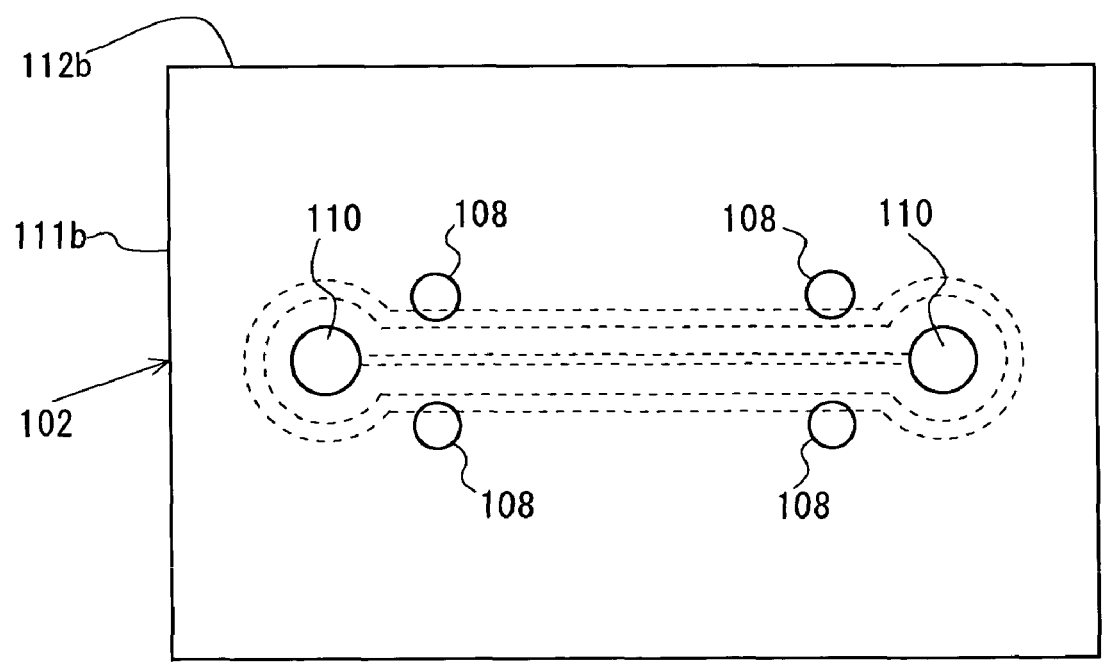
FIG. 38 is a plan view of a lid member in the ninth preferred embodiment of a plate assembly according to the present invention.
Figure 39:
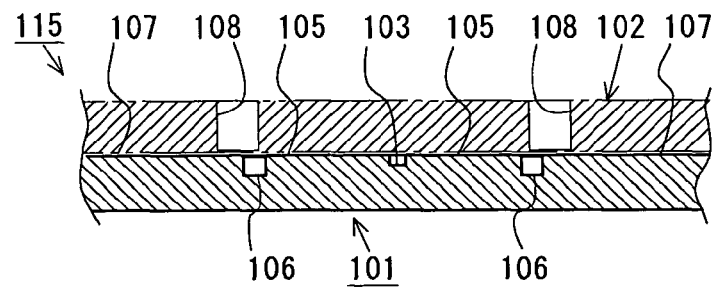
FIG. 39 is a sectional view taken along line XXXIX-XXXIX of FIG. 37.
Figure 40A:
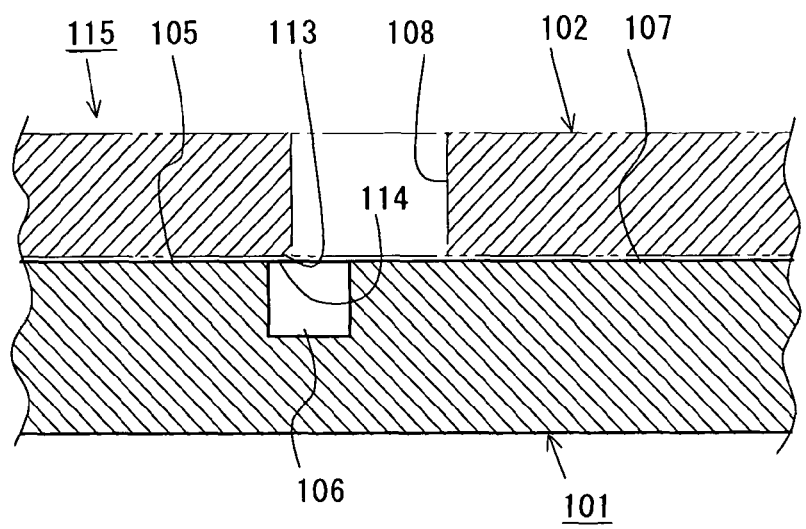
FIG. 40A is an enlarged view of a part of FIG. 39.
Figure 40B:
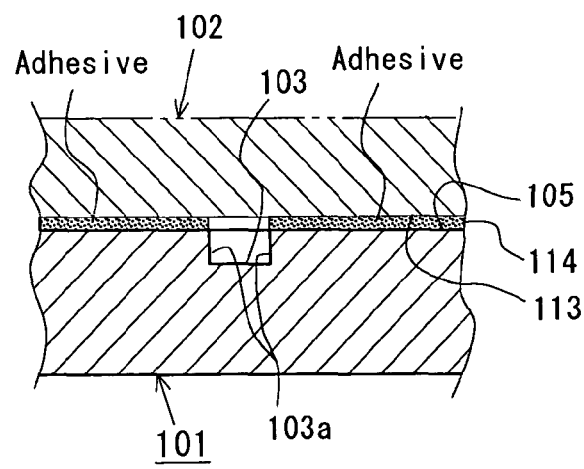
FIG. 40B is a sectional view taken along line XXXXB-XXXXB of FIG. 37.

FIGS. 37 through 40B show the ninth preferred embodiment of a plate assembly according to the present invention. FIG. 37 is a plan view of a plate member 101 in the ninth preferred embodiment. In FIG. 37, a lid member 102 bonded to the plate member 101 is also shown by dotted lines. FIG. 38 is a plan view of the lid member 102, and FIG. 39 is a sectional view taken along line XXXIX-XXXIX of FIG. 37. FIG. 40A is an enlarged sectional view showing a part of FIG. 39, and FIG. 40B is a sectional view taken along line XXXXB-XXXXB of FIG. 37.

The plate member 101 and the lid member 102 are formed of, e.g. polycarbonate (PC), and are preferably formed of the same material. If the plate member 101 and the lid member 102 are formed of the same material, the surface charge of the plate member 101 can be the same as that of the lid member 102, so that the electroosmosis flow to a sample during electrophoresis can be uniform to allow the flow of the sample to be constant. In addition, if the plate member 101 and the lid member 102 are formed of the same material, the behavior of a filler, which will be described later, toward the plate member 101 is the same as that toward the lid member 102, so that the movement of the filler due to capillarity is smooth.

The plate member 101 has an elongated linear fine groove (recessed portion) 103 in its substantially central portion. This fine groove 103 has a substantially square cross section (e.g. a square cross section, one side of which has a length of 5 to 1000 micrometers) and an overall length of a few centimeters. In both end portions of the fine groove 103, circular sample receiving holes (recessed portions) 104 are formed. The sample receiving holes 104 are communicated with the fine groove 103 (see FIG. 37). Around the sample receiving holes 104 and the fine groove 103, a sealing surface 105 is formed so as to surround the sample receiving holes 104 and the fine groove 103. A lid member fixing surface 107 is formed around the sealing surface 105 via a pass partition groove 106. In this preferred embodiment, the sealing surface 105 is substantially arranged on the same plane as that of the lid member fixing surface 107. As shown in FIGS. 39 and 40B, the fine groove 103 has a square cross section, one side of which has a length of 0.3 millimeters in this preferred embodiment. As shown in FIGS. 39 and 40A, the pass partition groove 106 has a square cross section, one side of which has a length of one millimeter.

The lid member 102 is a plate member substantially having the same plane size as that of the plate member 101. A pair of filler injecting holes 108 are formed in the lid member 102 on the side of each of both end portions of the fine groove 103. The filler injecting holes 108 are arranged outside of the sealing surface 105 of the plate member 101, and part of each of the filler injecting holes 108 is designed to be open to the pass partition groove 106. The pair of filler injecting holes 108 on the side of one end of the fine groove 103, and the pair of filler injecting holes 108 on the side of the other end of the fine groove 103 are formed symmetrically with respect to the fine groove 103, respectively. The lid member 102 also has a pair of through holes 110 corresponding to the sample receiving holes 104 of the plate member 101.

According to this preferred embodiment with such a construction, an adhesive is applied on the lid member fixing surface 107 of the plate member 101 and on a part of the lid member 102 corresponding to the lid member fixing surface 107. Furthermore, in this preferred embodiment, the adhesive has an excellent adhesive property to polypropylene (PP) being a material which is difficult to be adhesive. For example, a cyanoacrylate adhesive is used and applied to a portion, the surface of which has been primer-processed by an organic amine primer. Then, the first side 111*b* of the lid member 102 of FIG. 38 is aligned with and arranged on the first side 111*a* of the plate member 101 of FIG. 37, and the second side 112*b* of the lid member 102 of FIG. 38 is aligned with and arranged on the second side 112*a* of the plate member 101 of FIG. 37. In this state, the plate member 101 and the lid member 102 are held by a gripping means (not shown) to bond and fix the lid member 102 to the plate member 101. Then, a filler is injected into the filler injecting holes 108. This filler preferably has a small coefficient of viscosity so as to be suited to utilize capillarity which will be described later. If it takes a lot of time to harden the filler, there is some possibility that the filler flowing onto the sealing surface 105 may move, so that the hardening time of the filler is preferably short. For example, ultraviolet curable adhesive 3042 (trade name) produced by Three Bond is preferably used. Furthermore, the first side 111*a* and second side 112*a* of the plate member 101, and the first side 111*b* and second side 112*b* of the lid member 102 serve as reference surfaces when the plate member 101 and the lid member 102 are aligned with and fixed to each other. The first sides 111*a* and 111*b* are substantially perpendicular to the second sides 112*a* and 112*b*.

As shown in FIG. 40A, when the filler injected into the filler injecting holes 108 collects in the pass partition groove 106 to reach a fine gap 114 between the sealing surface 105 of the plate member 101 and the bottom face 113 of the lid member 102, the filler rapidly permeates the fine gap 114 due to capillarity. At this time, as shown in FIG. 40B, since the filler is designed to permeate the fine gap 114 between the sealing surface 105 of the plate member 101 and the bottom surface 113 of the lid member 102 due to capillarity, the filler does not enter the fine groove 103, in which the gap between the plate member 101 and the lid member 102 abruptly increases, due to capillarity, and the filler permeates up to a portion just above the side walls 103*a* of the fine groove 103. As a result, as shown in FIG. 40B, the sectional shape of the fine groove 103 can be precisely a desired rectangular sectional shape. Furthermore, it is considered that, if the plate member 101 and the lid member 102 are formed by the injection molding, the surface property of an injection molding die is transferred to the surfaces of the plate member 101 and lid member 102 to form the fine gap 114 of a few microns between the sealing surface 105 of the plate member 101 and the lid member 102 to cause capillarity by the fine gap 114.

If the lid member 102 is thus mounted on the plate member 101, a capillary electrophoresis chip (micro chip) 115 is formed. Then, the fine groove 103 of the capillary electrophoresis chip 115 is filled with a medium for separation, such as a buffer solution for electrophoresis or a polymer for molecular sieving, which is fed from one of the through holes 110 of the lid member 102, and a sample is fed into one end of the fine groove 103 from the other through hole 110 of the lid member 102. Thereafter, a high voltage is applied to both ends of the fine groove 103 to move the sample in the fine groove 103. By the difference in charge or molecular weight, a specific material is separated from the sample. The separated specific material is detected by ultraviolet absorption or fluorescence.

As described above, according to this preferred embodiment, the sealing surface 105 formed so as to surround the fine groove 103 and sample receiving holes 104 is separated by the pass partition groove 106 from the lid member fixing surface 107 formed so as to surround the sealing surface 105. Therefore, the lid member 102 is fixed to the lid member fixing surface 107 with the adhesive, and even if excessive part of the adhesive enters the pass partition groove 106, the pass partition groove 106 functions as a dam for the adhesive, so that the excessive part of the adhesive is collected in the pass partition groove 106. Thus, the adhesive does not pass over the sealing surface 105 to enter the fine groove 103 and the sample receiving holes 104, so that the fine groove 103 and the sample receiving holes 104 are not filled up with the adhesive and their sectional shapes are not deformed by the adhesive. In addition, according to this preferred embodiment, as shown in FIG. 40B, since the filler is designed to permeate the fine gap 114 between the sealing surface 105 and the lid member 102 due to capillarity, the filler does not enter the fine groove 103 and sample receiving holes 104, in which the gap between the plate member 101 and the lid member 102 abruptly increases, and the filler permeates up to a portion just above the side wall 103*a* of the fine groove 103. Therefore, if the plate assembly formed by bonding the lid member 102 to the plate member 101 at a predetermined position in this preferred embodiment is used as a capillary electrophoresis chip 115, the movement of the sample in the fine groove 103 due to electrophoresis is not prevented by the filler.

According to this preferred embodiment, since the filler can surely permeate the gap between the sealing surface 105 of the plate member 101 and the lid member 102 due to capillarity, the sample does not leak between the plate member 101 and the lid member 102 even if a pressure is applied into the fine groove 103 to carry out a test or the like.

According to this preferred embodiment, the filler does not enter the fine groove 103, in which the gap between the plate member 101 and the lid member 102 abruptly increases, due to capillarity, and the filler permeates up to a portion just above the side walls 103*a* of the fine groove 103. Therefore, the sectional shape of the passage for the sample can be uniformly ensured as designed (it is possible to prevent the cross-sectional area of the passage for the sample from varying), so that the flow of the sample can be stabilized to improve the precision of test.

According to this preferred embodiment, the lid member 102 is bonded and fixed to the plate member 101 with the adhesive, and the fine groove 103 is sealed with the filler permeating the fine gap 114, so that the following advantageous effects can be obtained.

That is, in order to bond and fix the lid member 102 to the plate member 101, it is possible to suitably select an adhesive having a good bonding strength to the resin material of the plate member 101 and lid member 102. Therefore, for example, even if the plate member 101 and the lid member 102 are formed of a resin material, such as polypropylene, which is difficult to be adhesive, the bonding strength of both members bonded to each other can be sufficiently high. Since the bonding strength of the lid member 102 to the plate member 101 can be sufficiently high regardless of the kind of the resin material, a material easy to be filled can be selected as the filler filled in the fine gap 114, which is defined by the sealing surface 105 of the plate member 101 and the bottom face 113 of the lid member 102, without sufficiently considering the adhesive property to the plate member 101 and lid member 102.

While the plate member 101 and the lid member 102 have been formed of polypropylene (PP) having an excellent chemical resistance in this preferred embodiment, the present invention should not be limited thereto, but the plate member 101 and the lid member 102 may be formed of polycarbonate (PC), polymethyl methacrylate (PMMA), ultraviolet curable resin, glass or the like. While the adhesive for fixing the lid member 102 to the plate member 101 has been formed of cyanoacrylate as an example in this preferred embodiment, the present invention should not be limited thereto, but the material of the adhesive may be suitably selected in accordance with the materials of the plate member 101 and lid member 102. While the ultraviolet curable adhesive has been used as an example of the filler, the present invention should not be limited thereto, but the material of the filler may be a material which is capable of permeating the fine gap 114 due to capillarity to be filled up to a portion just above the side wall 103a of the fine groove 103 and which has such an adhesive property (the bonding strength of the lid member 102 to the plate member 101) that a gap is not formed by a small variation in size of the fine gap 114.

While the filler has been injected onto the sealing surface 105 after bonding and fixing the lid member 102 to the plate member 101 in this preferred embodiment, the present invention should not be limited thereto, but the lid member 102 may be bonded and fixed to the plate member 101 by injecting the adhesive onto the lid member fixing surface 107 after allowing the injection and permeation of the filler onto the sealing surface 105 while the plate member 101 and the lid member 102 are held by a gripping means.

In this preferred embodiment, the filler has been allowed to permeate the gap between the sealing surface 105 of the plate member 101 and the lid member 102 due to capillarity. However, if the fine groove 103 is relatively large and if it is not required to carry out such a precise operation that the filler is allowed to permeate the gap between the sealing surface 105 of the plate member 101 and the lid member 102 due to capillarity, a very thin resin film may be sandwiched between the sealing surface 105 of the plate member 101 and the lid member 102, or such an amount of filler as not to protrude toward the fine groove 103 may be provided between the sealing surface 105 of the plate member 101 and the lid member to fill up the gap between the members 101 and 102. Thus, it is possible to prevent the sample from leaking from the fine groove 103, and the plate member 101 and lid member 102 which are difficult to be adhesive can be aligned with and fixed to each other.

Figure 41:
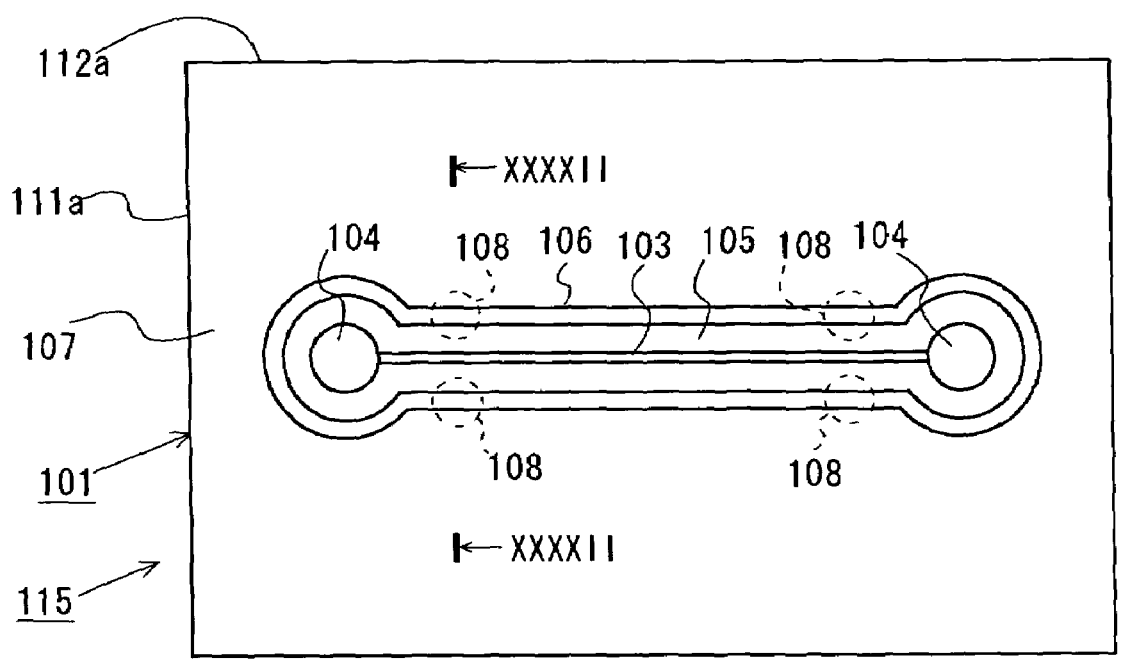
FIG. 41 is a plan view of a first modified example of the ninth preferred embodiment of a plate assembly according to the present invention.
Figure 42:
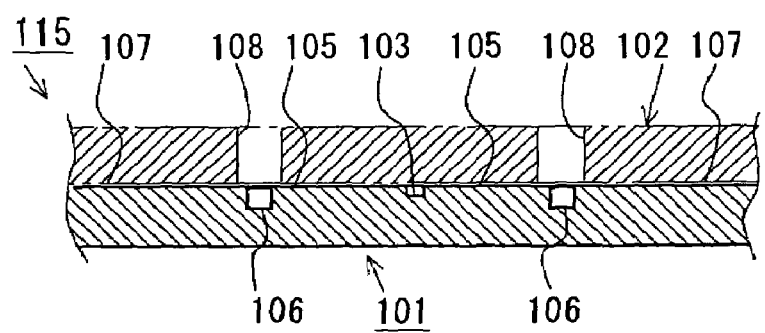
FIG. 42 is a sectional view taken along line XXXXII-XXXXII of FIG. 41.

FIGS. 41 and 42 show a first modified example of the ninth preferred embodiment of a plate assembly according to the present invention.

In this example, the plate assembly has the same construction as that in the above described ninth preferred embodiment, except that the positions of the filler injecting holes 108 are different from those in the ninth preferred embodiment. That is, in this example, the filler injecting holes 108 are open to the sealing surface 105, pass partition groove 106 and lid member fixing surface 107 of the plate member 101.

According to this example with such a construction, if the filler is dropped from the filler injecting holes 108, the filler dropped onto the sealing surface 105 permeates the fine gap 114 between the sealing surface 105 of the plate member 101 and the lid member 102 due to capillarity, and excessive part of the filler flows into the pass partition groove 106, or the filler dropped into the pass partition groove 106 permeates the fine gap 114 between the sealing surface 105 of the plate member 101 and the lid member 102 due to capillarity. Therefore, this example can obtain the same advantageous effects as those in the above described ninth preferred embodiment.

Figure 43:
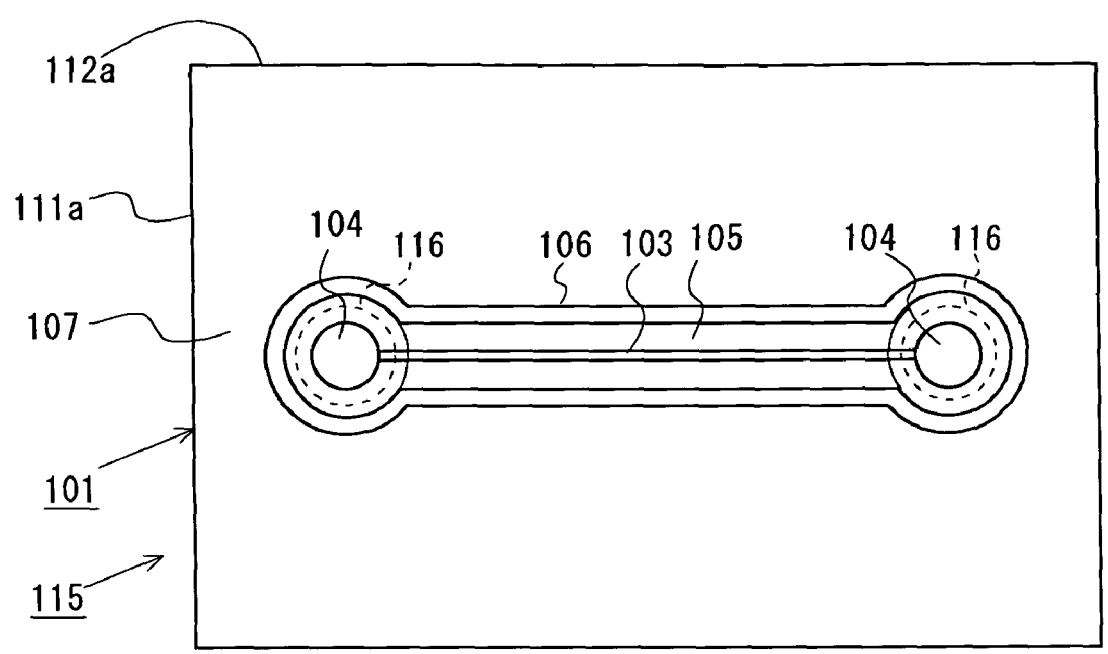
FIG. 43 is a plan view of a second modified example of a plate member in the ninth preferred embodiment of a plate assembly according to the present invention.
Figure 44:
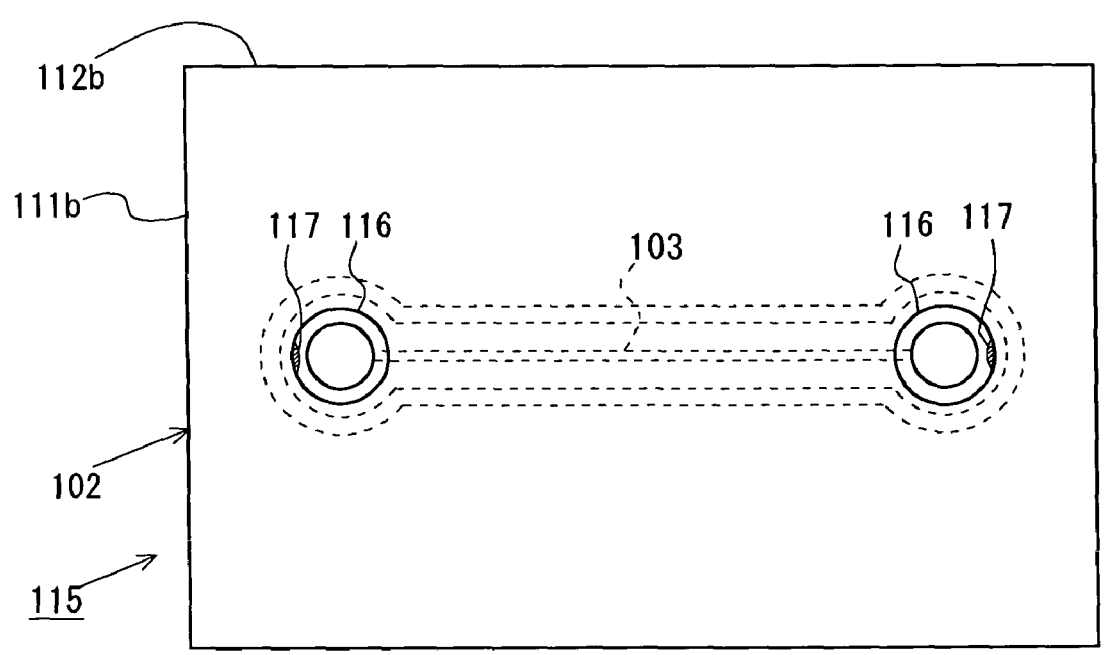
FIG. 44 is a plan view of a lid member bonded to the plate member of FIG. 43.

FIGS. 43 and 44 show a second modified example of the ninth preferred embodiment of a plate assembly according to the present invention.

In this example, the through holes 116 of the lid member 102 open to both end portions of the fine groove 103 are also used as filler injecting holes. In this example, when the filler is dropped from the through holes 116, target dropped regions are preferably regions (regions 117 shown by slant lines in FIG. 44) which are positioned above the sealing surface 105 on the opposite side to the fine groove 103 and which extend along the walls of the through holes 116. If the filler is dropped in such regions, the dropped filler permeates the fine gap 114 between the sealing surface 105 and the lid member 102 due to capillarity, so that it is possible to prevent the filler from entering the fine groove 103. Furthermore, the through holes 116 of the lid member 102 have such a size as to be capable of ensuring the sufficiently large sealing surface 105 around the sample receiving holes 104, and have a greater diameter than that of the sample receiving holes 104.

Figure 45:
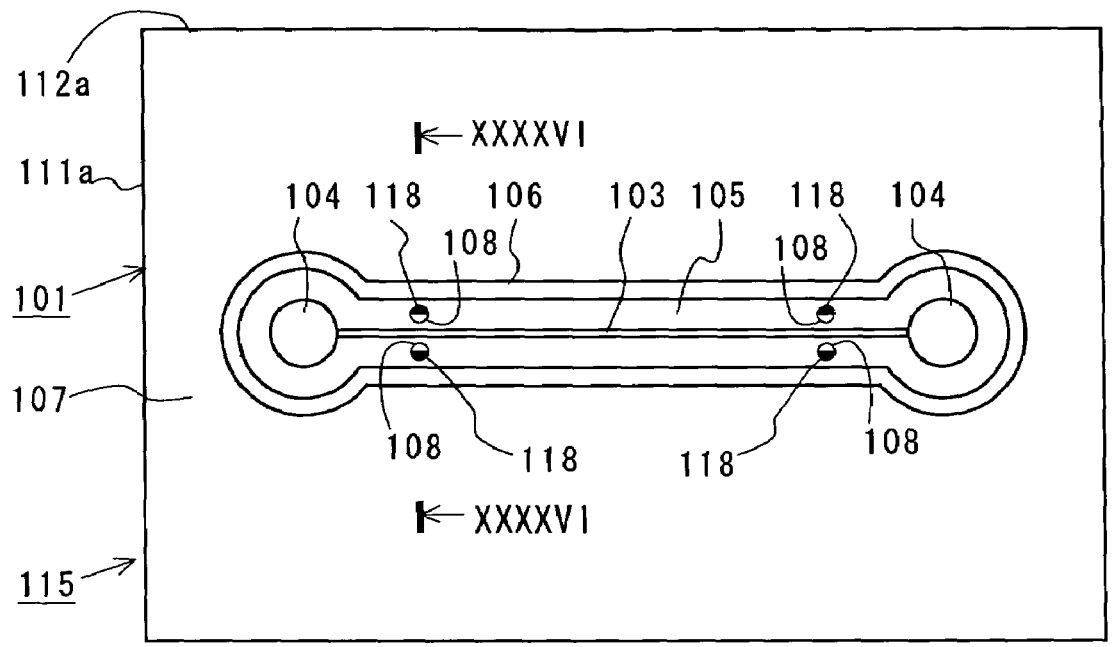
FIG. 45 is a plan view of a third modified example of the ninth preferred embodiment of a plate assembly according to the present invention.
Figure 46:
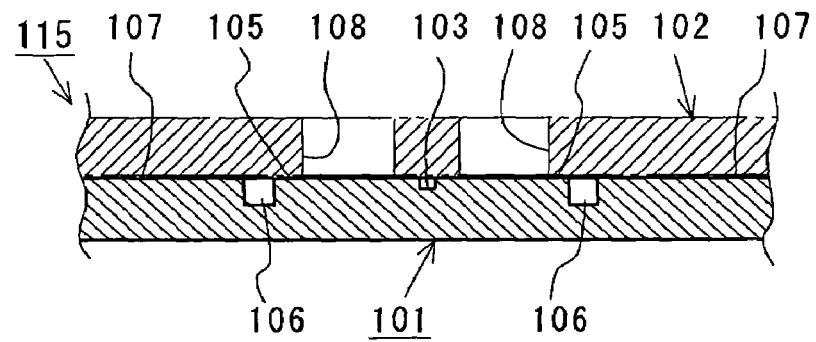
FIG. 46 is a sectional view taken along line XXXXVI-XXXXVI of FIG. 45.

FIGS. 45 and 46 show a third modified example of the ninth preferred embodiment of a plate assembly according to the present invention.

In this example, the plate assembly has the same construction as that in the ninth preferred embodiment, except that the positions of the filler injecting holes 108 are different from those in the above described ninth preferred embodiment. That is, in this example, the filler injecting holes 108 are open to the sealing surface 105 of the plate member 101.

According to this example with such a construction, if the filler is dropped from the filler injecting holes 108 after the lid member 102 is bonded and fixed to the lid member fixing surface 107 of the plate member 101, the filler dropped onto the sealing surface 105 permeates the fine gap 114 between the sealing surface 105 of the plate member 101 and the lid member 102 due to capillarity. Therefore, this example can obtain the same advantageous effects as those in the above described ninth preferred embodiment. Furthermore, when the filler is injected into the filler injecting holes 108, the filler is preferably dropped into portions (black-painted portions 118) of the filler injecting holes 118 far away from the fine groove 103 as shown in FIG. 45. Thus, even if the lid member 102 and the plate member 101 are assembled by mistake so that the filler injecting holes 108 are displaced toward the fine groove 103, it is possible to prevent the filler from flowing directly into the fine groove 103.

Figure 47:
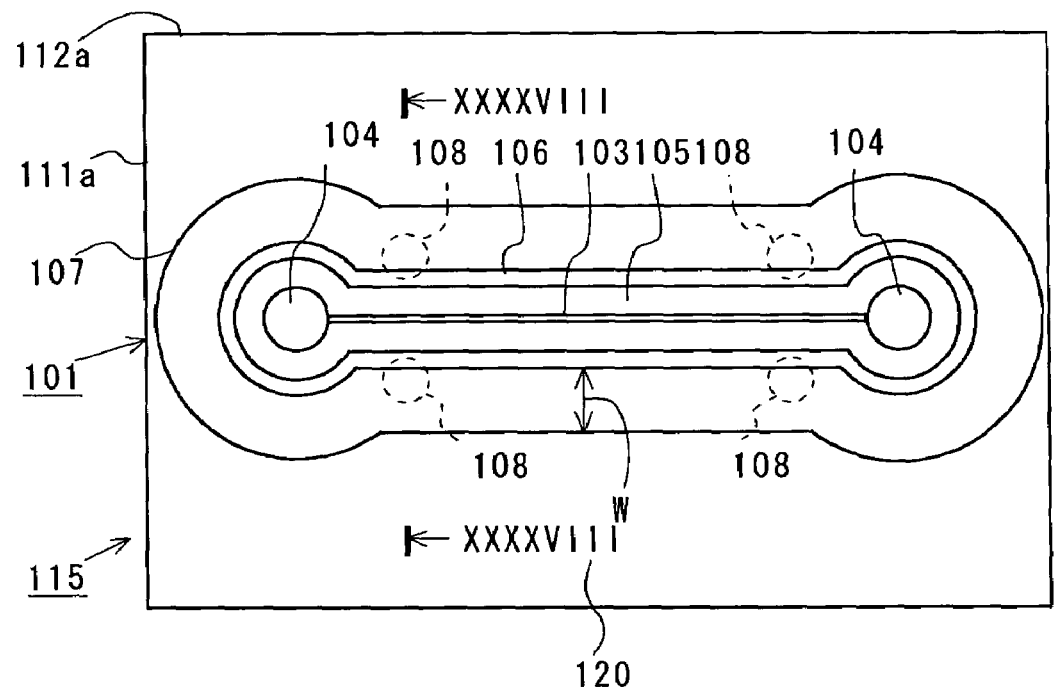
FIG. 47 is a plan view of a fourth modified example of the ninth preferred embodiment of a plate assembly according to the present invention.
Figure 48:
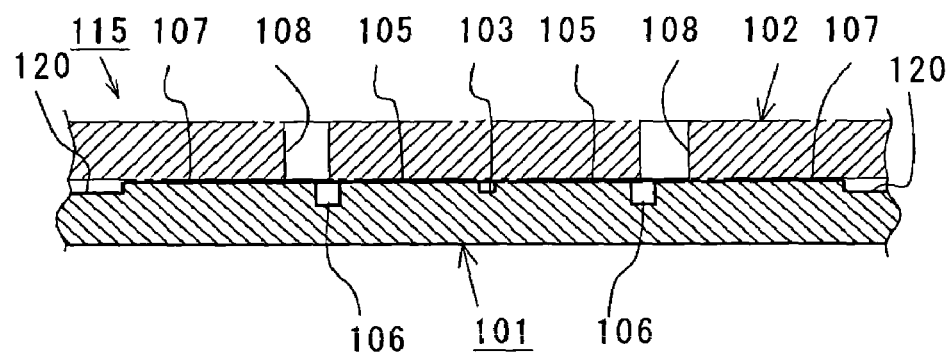
FIG. 48 is a sectional view taken along line XXXXVIII-XXXXVIII of FIG. 47.

FIGS. 47 and 48 show a fourth modified example of the ninth preferred embodiment of a plate assembly according to the present invention.

In this example, the plate assembly has the same construction as that in the above described ninth preferred embodiment, except that the lid member fixing surface 107 having a predetermined width is formed so as to surround the sealing surface 105 and that a fixing relief portion 120 is formed outside of the lid member fixing surface 107 so that the area of the adhesive to be applied is small. Furthermore, the fixing relief portion 120 of the plate member 101 should be slightly recessed from the lid member fixing surface 107 so as not to contact the lid member 102. The width W of the lid member fixing surface 107 is suitably determined in accordance with design conditions for the plate member 101 if it is possible to obtain a bonding strength sufficient for the fixing of the lid member 102 to the plate member 101.

Figure 49:
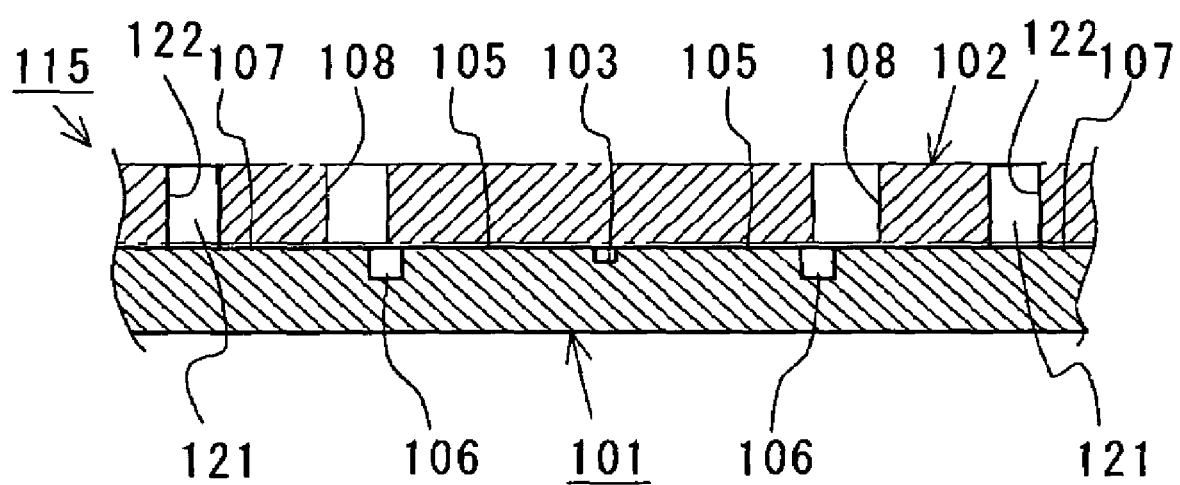
FIG. 49 is a sectional view for explaining a fifth modified example of the ninth preferred embodiment of a plate assembly according to the present invention.

FIG. 49 shows a fifth modified example of the ninth preferred embodiment of a plate assembly according to the present invention.

In this example, unlike the above described ninth preferred embodiment wherein the lid member 102 is bonded and fixed to the plate member 101, the lid member 102 is mounted on and fixed to the plate member 101 by melting and caulking the tips of a plurality of substantially cylindrical protrusions 121, which are formed on the lid member fixing surface 107 of the plate member 101, after causing the protrusions 121 to be fitted into engaging holes 122 of the lid member 102.

According to this example with such a construction, the lid member 102 can be surely fixed to the plate member 101 if it is difficult for the materials of the plate member 101 and lid member 102 to be bonded and fixed to each other. In addition, according to this example, the protrusions 121 of the plate member 101 can function as positioning pins, so that the lid member 102 can be precisely positioned and fixed to the plate member 101.

Furthermore, in this example, the protrusions 121 are formed on the plate member 101, and the engaging holes 122 are formed in the lid member 102. However, the present invention should not be limited thereto. The protrusions 121 may be formed on at least one of the plate member 101 and the lid member 102, and the engaging holes 122 may be formed in the other of the plate member 101 and the lid member 102. The positions of the protrusions 121 and engaging holes 122 are suitably determined in accordance with the shape of the fine groove 103 and space above the plate member 101. However, in order to enhance the fixing strength of the lid member 102 to the plate member 101 in the vicinity of the fine groove 103, the protrusions 121 and engaging holes 122 are preferably determined so as to be positioned in the vicinity of the pass partition groove 106 of the lid member fixing surface 107.

Tenth Preferred Embodiment

FIGS. 50 through 53C show the tenth preferred embodiment of a plate assembly according to the present invention. In this preferred embodiment, a plurality of spacer protrusions 131 are formed at appropriate intervals on at least one of the sealing surface 105 of the plate member 101 and the face (bottom face) 113 of the lid member 102 facing the sealing surface 105.

Figure 50:
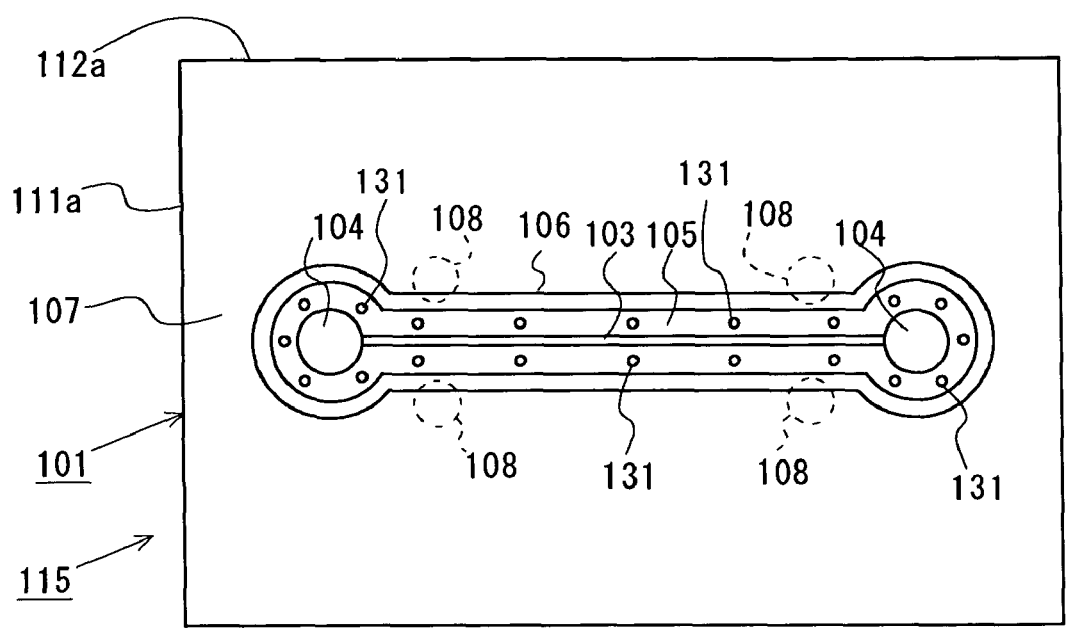
FIG. 50 is a plan view of a plate member in the tenth preferred embodiment of a plate assembly according to the present invention.
Figure 51:
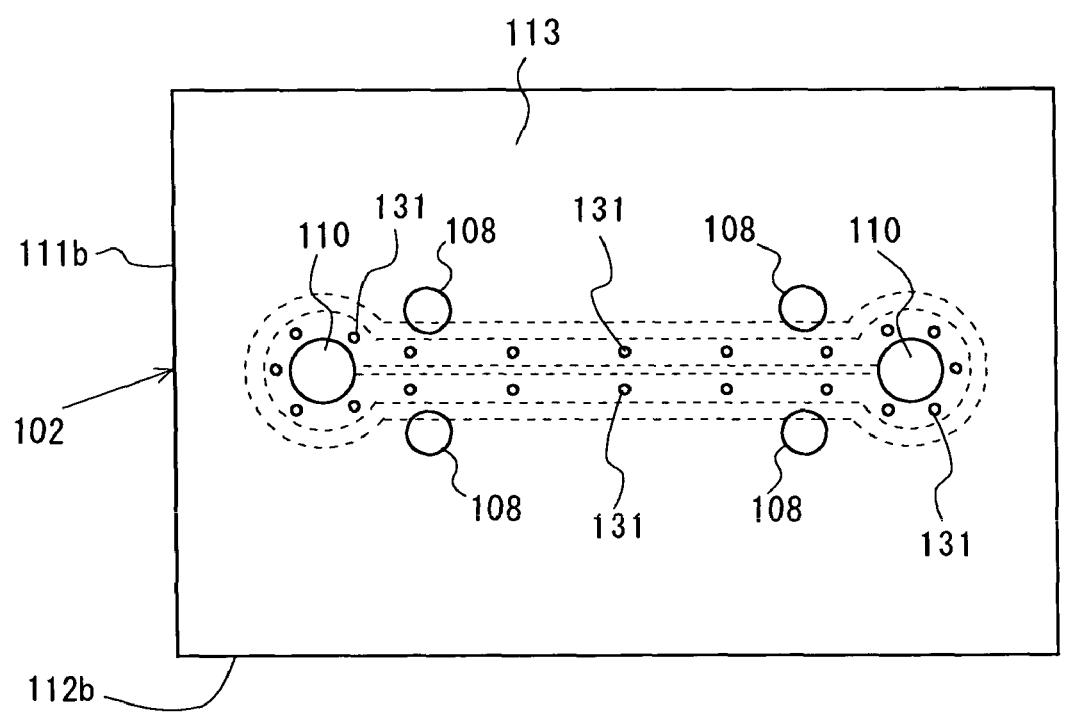
FIG. 51 is a plan view of a lid member in the tenth preferred embodiment of a plate assembly according to the present invention.
Figure 52:
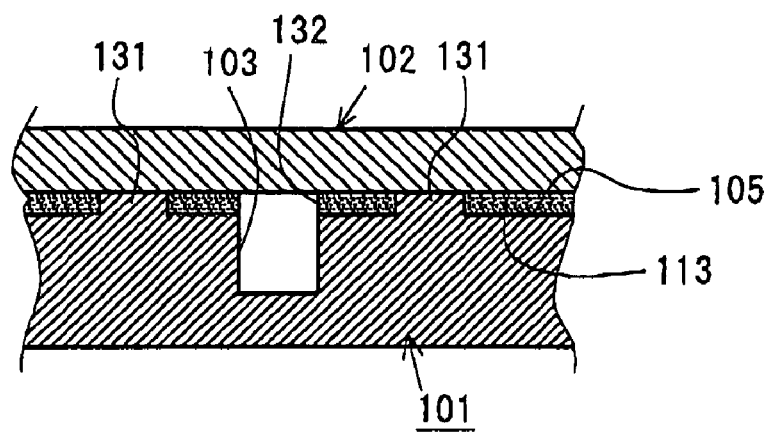
FIG. 52 is a sectional view of a built-up structure in the tenth preferred embodiment of a plate assembly according to the present invention, which is taken along a line perpendicular to a fine groove.

For example, FIG. 50 shows the plurality of spacer protrusions 131 formed at appropriate intervals on the sealing surface 105 of the plate member 101. FIG. 52 shows a state that the lid member 102 is aligned with and bonded to the plate member 101 having the spacer protrusions 131 so that the first side 111$b$ of the lid member 102 of FIG. 51 is aligned with and arranged on the first side 111$a$ of the plate member 101 of FIG. 50 and so that the second side 112$b$ of the lid member 102 of FIG. 51 is aligned with and arranged on the second side 112$a$ of the plate member 101 of FIG. 50. As shown in FIG. 52, if the spacer protrusions 131 formed on the sealing surface 105 of the plate member 101 contact the facing lid member 102, a gap can be formed between the sealing surface 105 of the plate member 101 and the lid member 102 so that a filler 132 can permeate the gap due to capillarity. That is, the spacer protrusions 131 formed on the sealing surface 105 of the plate member 101 have such a height that the filler 132 can permeate the gap between the sealing surface 105 of the plate member 101 and the lid member 102 due to capillarity.

Figure 53A:
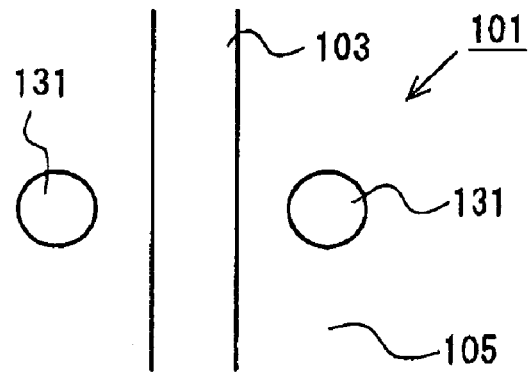
FIG. 53A is a plan view showing the relationship between spacer protrusions and a fine groove in the tenth preferred embodiment of a plate assembly according to the present invention.
Figure 53B:
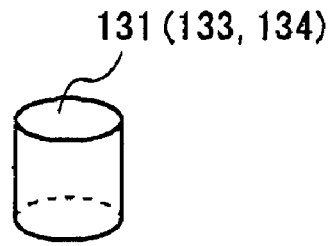
FIG. 53B is a perspective view of an example of a spacer protrusion in the tenth preferred embodiment of a plate assembly according to the present invention.
Figure 53C:
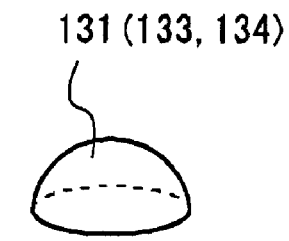
FIG. 53C is a perspective view of another example of a spacer protrusion in the tenth preferred embodiment of a plate assembly according to the present invention.

FIG. 53A shows the relationship between the fine groove 103 and the spacer protrusions 131 formed on the sealing surface 105 of the plate member 101, and FIGS. 53B and 53C show the shape of one of the spacer protrusions 131 formed on the sealing surface 105 of the plate member 101. For production, the spacer protrusion 131 is preferably cylindrical as shown in FIG. 53B or substantially hemispherical as shown in FIG. 53C. The shape of the spacer protrusion 131 should not be limited thereto, but it may be a truncated cone or another space.

FIG. 51 shows an embodiment wherein a plurality of spacer protrusions 131 shown in FIG. 53B or 53C are formed at appropriate intervals on the bottom face 113 of the lid member 102 bonded to the plate member 101. Alternatively, the spacer protrusions 131 may be formed on the sealing surface 105 of the plate member 101 as shown in FIG. 50, and the spacer protrusions 131 may be formed on the bottom face 113 of the lid member 102 bonded to the plate member 101, so that the spacer protrusions 131 may butt the facing member to form such a gap between the sealing surface 105 of the plate member 101 and the lid member 102 that the filler 132 can permeate the gap due to capillarity.

Figure 54:
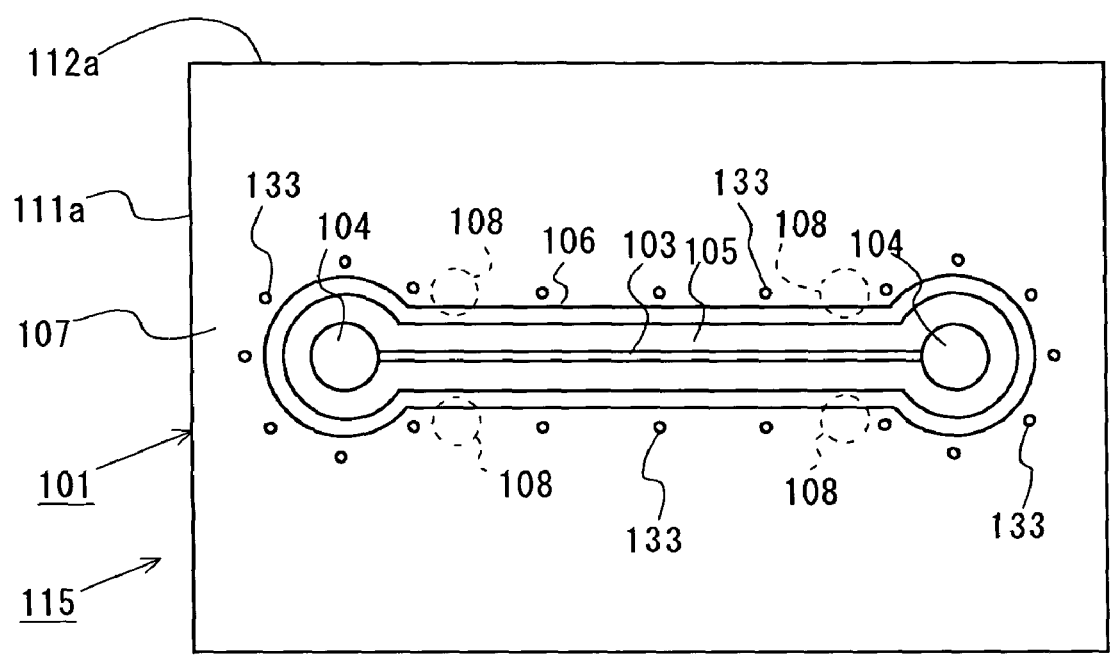
FIG. 54 is a plan view of a first modified example of a plate member in the tenth preferred embodiment of a plate assembly according to the present invention.
Figure 55:
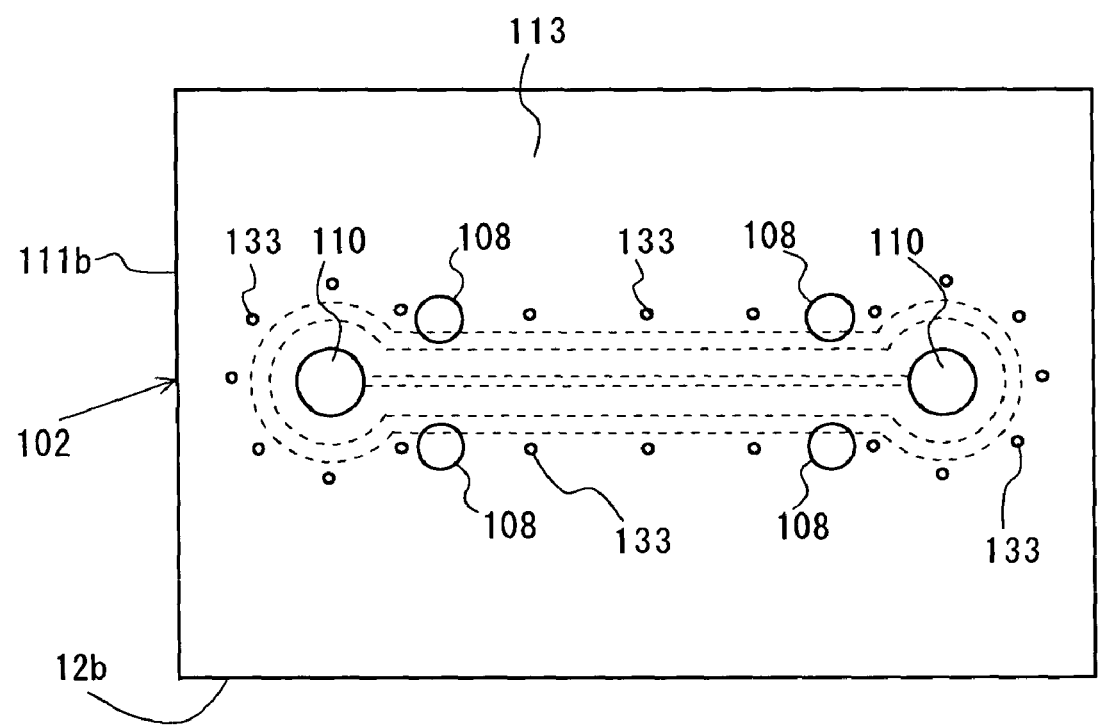
FIG. 55 is a plan view of a first modified example of a lid member in the tenth preferred embodiment of a plate assembly according to the present invention.

FIGS. 54 and 55 show a first modified example of the tenth preferred embodiment of a plate assembly according to the present invention. In this example, as shown in FIG. 54, a plurality of spacer protrusions 133 are formed at appropriate intervals on the lid member fixing surface 107 of the plate member 101. As described in the ninth preferred embodiment, the lid member fixing surface 107 of the plate member 101 is a portion which is formed around the sealing surface 105 so as to be separated by the fine groove 103 and which is formed substantially on the same plane as that of the sealing surface 105. Therefore, the spacer protrusions 133 formed on the lid member fixing surface 107 of the plate member 101 are formed so as to substantially have the same height as that of the spacer protrusions 131 formed on the sealing surface 105 (see FIGS. 50 and 52). As a result, if the lid member 102 is arranged on the plate member 101 so that the spacer protrusions 133 formed on the lid member fixing surface 107 of the plate member 101 butt the bottom face 113 of the lid member 102, a gap is formed between the sealing surface 105 of the plate member 101 and the lid member 102 so that the filler can permeate the gap due to capillarity.

Alternatively, as shown in FIG. 55, the plurality of spacer protrusions 133 may be formed at appropriate intervals on the face (bottom face) 113 of the lid member 102 facing the lid member fixing surface 107 of the plate member 101. In this case, similar to the case shown in FIG. 54, the height of the spacer protrusions 133 is the same as that of the spacer protrusions 133 formed on the lid member fixing surface 107. As a result, if the lid member 102 is arranged on the plate member 101 so that the spacer protrusions 133 formed on the bottom face 113 of the lid member 102 butt the lid member fixing surface 107 of the plate member 101, a gap is formed between the sealing surface 105 of the plate member 101 and the lid member 102 so that the filler can permeate the gap due to capillarity. Furthermore, the spacer protrusions 133 may be formed on both of the lid member fixing surface 107 of the plate member 101 and the lid member 102.

Figure 56:
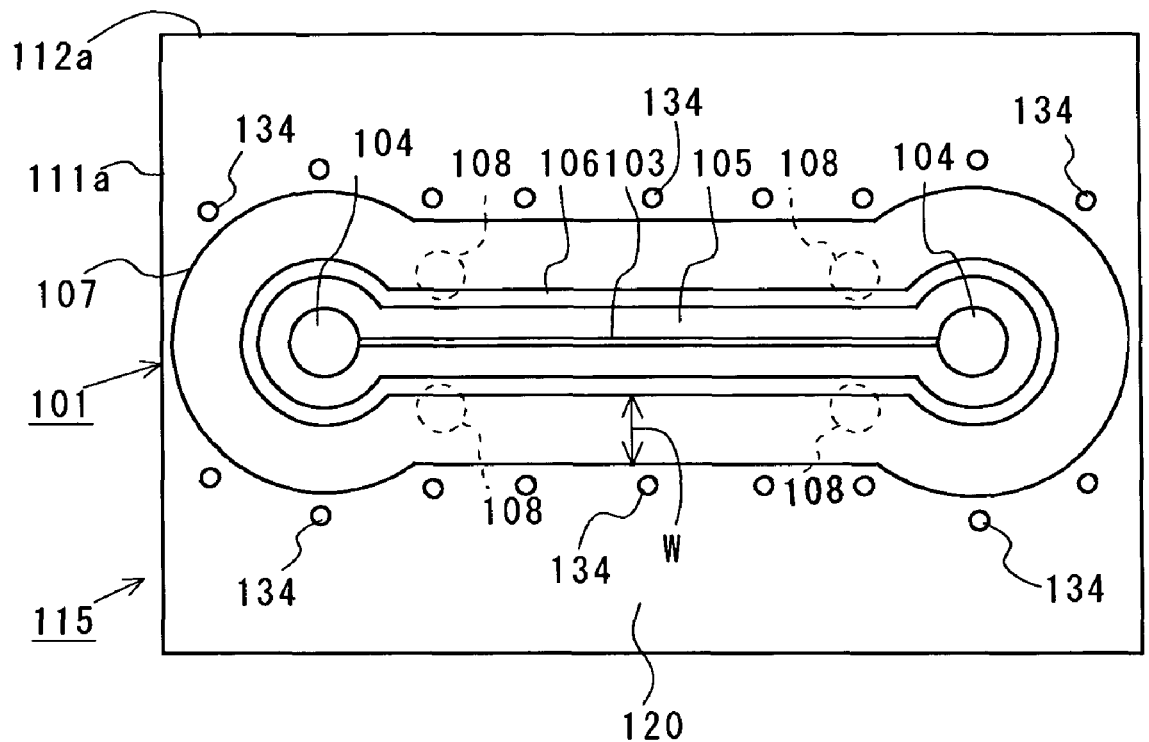
FIG. 56 is a plan view of a second modified example of the tenth preferred embodiment of a plate assembly according to the present invention.
Figure 57:
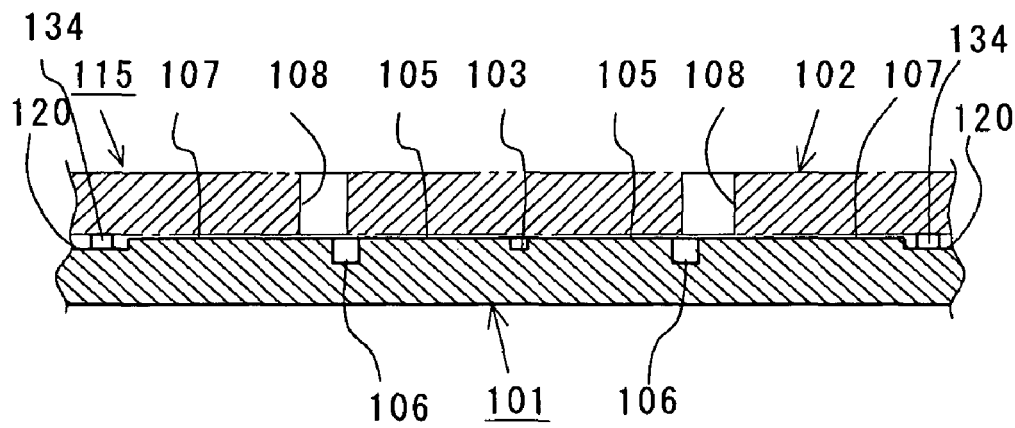
FIG. 57 is a sectional view of a built-up structure in the tenth preferred embodiment of a plate assembly according to the present invention, which is taken along a line perpendicular to a fine groove.
Figure 58:
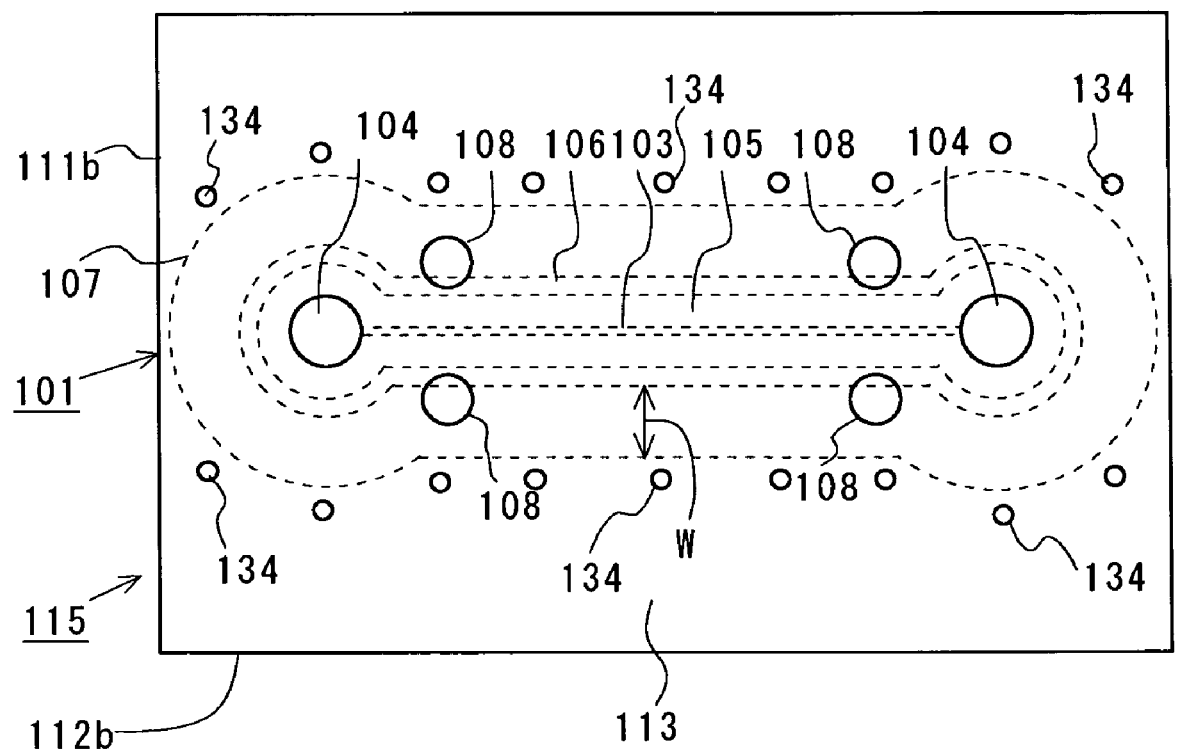
FIG. 58 is a bottom view of a second modified example of a lid member in the tenth preferred embodiment of a plate assembly according to the present invention.

FIGS. 56 through 58 show a second modified example of the tenth preferred embodiment of a plate assembly according to the present invention. In this example, as shown in FIG. 56, a plurality of spacer protrusions 134 are formed on the fixing relief portion 120 of the plate member 101 at appropriate intervals. As described in the ninth preferred embodiment, the fixing relief portion 120 of the plate member 101 is formed around the sealing surface 105 so as to be recessed. Therefore, the spacer protrusions 134 formed on the fixing relief portion 120 of the plate member 101 are formed so as to be longer by the depth of the fixing relief portion 120 recessed from the sealing surface 105 (see FIG. 57). As a result, if the lid member 102 is arranged on the plate member 101 so that the spacer protrusions 134 formed the fixing relief portion 120 of the plate member 101 butt the bottom face 113 of the lid member 102, a gap is formed between the sealing surface 105 of the plate member 101 and the lid member 102 so that the filler can permeate the gap due to capillarity.

Alternatively, as shown in FIG. 58, the spacer protrusions 134 may be formed at appropriate intervals on the face (bottom face) 113 of the lid member 102 facing the fixing relieve portion 120 of the plate member 101. In this case, similar to the case shown in FIG. 56, the spacer protrusions 134 are formed so as to be longer by the depth of the fixing relief portion 120 recessed from the sealing surface 105 and lid member fixing surface 107. As a result, if the lid member 102 is arranged on the plate member 101 so that the spacer protrusions 134 formed the bottom face 113 of the lid member 102 butt the fixing relief portion 120 of the plate member 101, a gap is formed between the sealing surface 105 of the plate member 101 and the lid member 102 so that the filler can permeate the gap due to capillarity. Furthermore, the spacer protrusions 134 may be formed on both of the fixing relief portion 120 of the plate member 101 and the lid member 102.

According to this preferred embodiment with such a construction, the spacer protrusions 131, 133 or 134 formed on at least one of the plate member 101 and the lid member 102 can form a gap between the sealing surface 105 of the plate member 101 and the lid member 102 so that the filler can permeate the gap due to capillarity. Therefore, even if the plate member 101 and/or the lid member 102 is deformed by warpage or the like, the plate member 101 and the lid member 102 can be aligned with each other to be held so as to rectify the deformation, such as warpage, so that it is possible to allow the filler to permeate the gap between the sealing surface 105 of the plate member 101 and the lid member 102 due to capillarity and it is possible to surely seal the portion surrounding the fine groove 103 of the plate member 101 (the gap between the plate member 101 and the lid member 102).

Eleventh Preferred Embodiment

Figure 59:
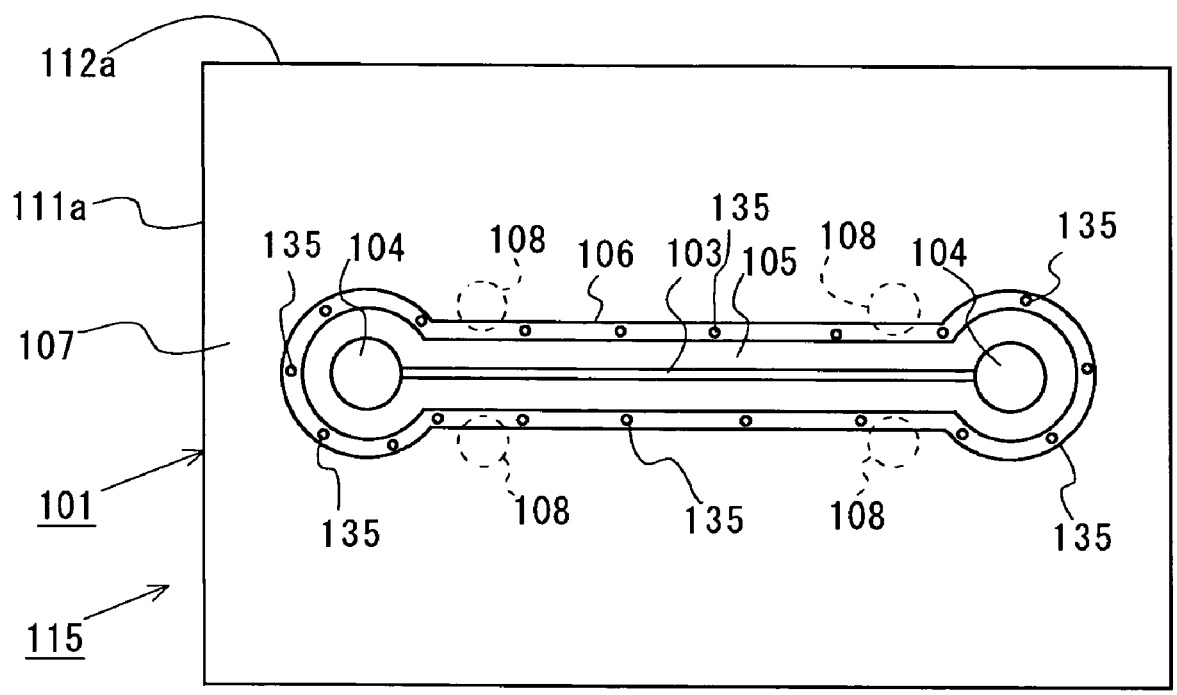
FIG. 59 is a plan view of a plate member in the eleventh preferred embodiment of a plate assembly according to the present invention.

FIG. 59 shows the eleventh preferred embodiment of a plate assembly according to the present invention. In this embodiment, spacers 135 are provided between the plate member 101 and the lid member 102 in the ninth preferred embodiment.

In FIG. 59, the pass partition groove 106 is formed in the lid member fixing surface 107 of the plate member 101 so as to surround the sealing surface 105. The pass partition groove 106 houses therein a plurality of spherical or cylindrical spacers 135. If the lid member (not shown) is aligned with and arranged on the plate member 101 housing therein the spacers 135, a gap is formed between the sealing surface 105 of the plate member 101 and the lid member so that a filler can permeate the gap due to capillarity.

In this preferred embodiment, a spacer housing groove surrounding the pass partition groove 106 may be formed to house therein the spacers 135.

In this preferred embodiment, the spacers 135 housed between the plate member 101 and the lid member can form the gap between the sealing surface 105 of the plate member 101 and the lid member so that the filler can permeate the gap due to capillarity. Therefore, even if the plate member 101 and/or the lid member is deformed by warpage or the like, the plate member 101 and the lid member can be aligned with each other to be held so as to rectify the deformation, such as warpage, so that it is possible to allow the filler to permeate the gap between the sealing surface 105 of the plate member 101 and the lid member due to capillarity and it is possible to surely seal the portion surrounding the fine groove 103 of the plate member 101 (the gap between the plate member 101 and the lid member).

According to this preferred embodiment, the spacers 135 are housed in the pass partition groove 106. Thus, the spacers 135 do not enter the fine groove 103 by mistake, and the spacers 135 do not fill up the fine groove 103. In addition, there is not some possibility that the spacers 135 fall away from the plate member 101.

Twelfth Preferred Embodiment

FIGS. 60A through 60D show examples of the twelfth preferred embodiment of a plate assembly according to the present invention, wherein the bonding strength of the lid member 102 to the plate member 101 is enhanced.

Figure 60A:
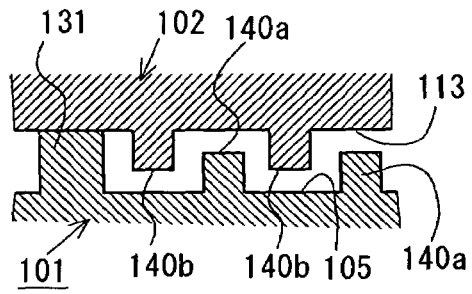
FIG. 60A is a sectional view of a first example of a built-up structure in the twelfth preferred embodiment of a plate assembly according to the present invention.

FIG. 60A shows an example where protrusions 140*a* and 140*b* having a lower height than that of the spacer protrusions 131 are formed on the sealing surface 105 of the plate member 101 and the facing bottom face 113 of the lid member 102, respectively, to align and arrange the lid member 102 with and on the plate member 101 so as to insert the protrusions 140*b* of the lid member 102 into spaces between the spacer protrusions 131 and protrusions 140*a* of the plate member 101 or between the protrusions 140*a* and 140*a* of the plate member 101. According to this example, a gap allowing the permeation of an adhesive filler is formed between the spacer protrusions 131 and the protrusions 140*b* or between the protrusions 140*a* and 140*b*, and the surface area of the filler contacting the plate member 101 and lid member 102 is greater than that in the above described ninth preferred embodiment of a plate assembly according to the present invention, so that the adhesion force of the lid member 102 to the plate member 101 increases to improve the sealing performance around the fine groove 3.

Figure 60B:
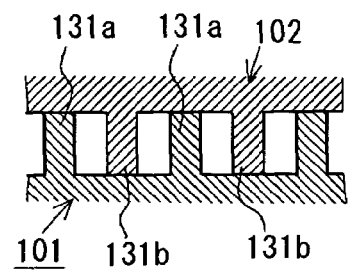
FIG. 60B is a sectional view of a second example of a built-up structure in the twelfth preferred embodiment of a plate assembly according to the present invention.

FIG. 60B shows an example where the lid member 102 is aligned with and arranged on the plate member 101 so as to insert the protrusions 131*b* of the lid member 102 into spaces between the spacer protrusions 131*a* and 131*a* of the plate member 101. According this example, a gap is formed between the spacer protrusions 131*a* and 131*b* so that a filler can permeate the gap due to capillarity, and the surface area of the filler contacting the plate member 101 and lid member 102 is greater than that in the above described ninth preferred embodiment of a plate assembly according to the present invention, so that the adhesion force of the lid member 102 to the plate member 101 can increase to improve the sealing performance around the fine groove 3.

Figure 60C:
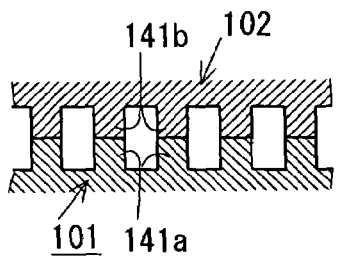
FIG. 60C is a sectional view of a third example of a built-up structure in the twelfth preferred embodiment of a plate assembly according to the present invention.

FIG. 60C shows an example where the lid member 102 is aligned with and arranged on the plate member 101 so that protrusions 141a formed between spacer protrusions (not shown) on the plate member 101 butt protrusions 141b formed on the lid member 102. According to this example, a gap is formed between the adjacent protrusions 141a and 141b so that a filler can permeate the gap due to capillarity, so that the surface area of the filler contacting the plate member 101 and lid member 102 is greater than that in the above described ninth preferred embodiment of a plate assembly according to the present invention. Therefore, the adhesion force of the lid member 102 to the plate member 101 increases, so that it is possible to improve the sealing performance around the fine groove 3. Furthermore, the protrusions 141a and 141b shown in this figure may be utilized as spacer protrusions.

Figure 60D:
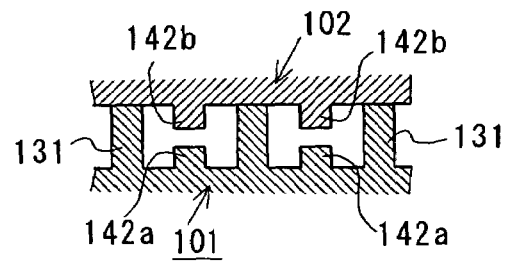
FIG. 60D is a sectional view of a fourth example of a built-up structure in the twelfth preferred embodiment of a plate assembly according to the present invention.

FIG. 60D shows an example where protrusions 142a being half or less than the height of the spacer protrusions 131 are formed between the spacer protrusions 131 and 131 of the plate member 101 and wherein 142b being substantially the same as the protrusions 142a are formed on the lid member 102. According to this example, since the protrusions 142a and 142b are arranged in spaces between the spacer protrusions 131 and 131, the surface area of the filler contacting the plate member 101 and lid member 102 is greater than that in the above described ninth preferred embodiment of a plate assembly according to the present invention. Therefore, the adhesion force of the lid member 102 to the plate member 101 increases, so that it is possible to improve the sealing performance around the fine groove 103.

Thirteenth Preferred Embodiment

Figure 61A:
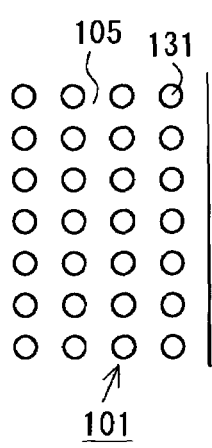
FIG. 61A is an enlarged plan view of an example of a part of the thirteenth preferred embodiment of a plate assembly according to the present invention, wherein spacer protrusions are arranged at substantially regular intervals.
Figure 61B:
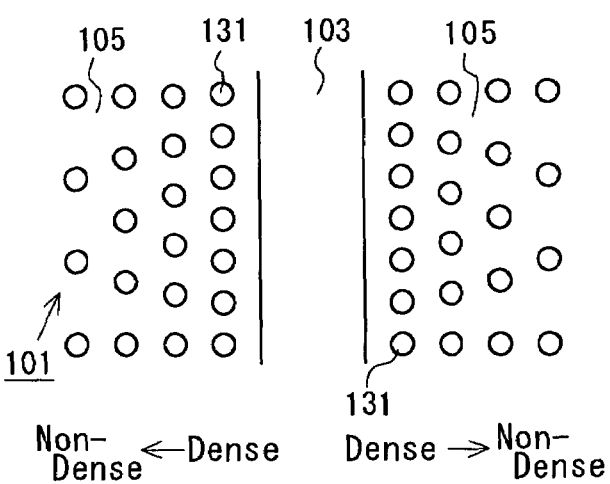
FIG. 61B is an enlarged plan view of another example of a part of the thirteenth preferred embodiment of a plate assembly according to the present invention, wherein the density of spacer protrusions varies.

FIGS. 61A and 61B show examples of arrangement of spacer protrusions 131 in the thirteenth preferred embodiment of a plate assembly according to the present invention.

FIG. 61A shows an example where a plurality of spacer protrusions 131 are formed on the sealing surface 105 at substantially regular intervals. FIG. 61B shows an example where the intervals of the spacer protrusions 131 formed on the sealing surface 105 vary from dense to non-dense as a distance from the fine groove 103 increases. According to the example shown in FIG. 61B, the flow resistance of a filler is lower on the far side from the fine groove 103, and the flow resistance of the filler is higher in the vicinity of the fine groove 103. As a result, according to the example shown in FIG. 61B, it is possible to more effectively prevent the filler from flowing into the fine groove 103.

As shown in FIGS. 61A and 61B, the nearest spacer protrusions 131 to the fine groove 103 are formed so as to be spaced from the fine groove 103 by a predetermined distance. With this construction, it is possible to prevent the filler, which permeates the gap between the sealing surface 105 of the plate member 101 and the lid member (not shown) due to capillarity, from protruding toward the fine groove 3.

Furthermore, the present invention should not be limited to the above described preferred embodiments wherein the lid member 102 is fixed to the plate member 101 (the embodiment wherein the lid member 102 is bonded and fixed to the plate member 101 (see FIGS. 37 through 40B) and the embodiment wherein the lid member 102 is fixed to the plate member 101 by caulking the protrusions 121 of the plate member 101 fitted into the engaging holes 122 of the lid member 102 (see FIG. 49)), but the lid member 102 may be fixed to the lid member fixing surface 107 of the plate member 101 by the ultrasonic welding, vibrating welding, laser beam welding or the like. In such an embodiment wherein the lid member 102 is fixed to the plate member 101 by the ultrasonic welding, vibrating welding, laser beam welding or the like, both of the lid member 102 and the plate member 101 are partially melted. However, since the melted and fixed portion is separated from the sealing surface 105 and fine groove 103 by the pass partition groove 106, there is no bad influence on the shape and precision of the fine groove 103 and sample receiving holes 104.

Furthermore, the sectional shape of the fine groove 103 should not be limited to that in the above described preferred embodiments, but the fine groove 103 may have another shape, such as semicircle, U-shape, or substantially triangle.

In addition, the sectional shape of the pass partition groove 106 should not be limited to that in the above described preferred embodiments, but the pass partition groove 106 may have another shape, such as semicircle, U-shape, or substantially triangle.

The plane shape of the fine groove 103 in the above described preferred embodiments should not be limited to be linear (see FIG. 37), but the present invention may be applied to a plate assembly having a fine groove 103 having cross, Y-shape, curve or another complicated shape. Of course, the present invention can be applied to a plate assembly having a fine groove 103 having a constant width and depth, but the invention may be applied to a plate assembly having a fine groove, the width and depth of which vary.

While the capillary electrophoresis chips 115 used for carrying out tests in the field of biochemistry have been described as examples for convenience of explanation in the above described preferred embodiments, the present invention should not be limited thereto, but the invention may be widely applied to a plate assembly which has a recessed portion for carrying out chemical tests in various fields other than the field of biochemistry, such as the fields of synthetic chemistry, physical chemistry and analytical chemistry.

As described above, according to the present invention, the sealing surface is formed so as to surround the recessed portion of the plate member, and the lid member is fixed to the lid member fixing surface, which is separated from the sealing surface by the pass partition groove, so as to allow the filler to permeate the fine gap between the sealing surface and the lid member due to capillarity, so that the filler permeates up to a portion just above the side walls of the recessed portion without flowing into the recessed portion while surely filling the filler in the fine gap between the sealing surface and the lid member. Therefore, according to the present invention, it is possible to bond the lid member to the plate member without deteriorating the shape and precision of the recessed portion of the plate member.

According to the present invention, the spacer protrusions formed on at least one of the plate member and the lid member can form the gap between the sealing surface of the plate member and the lid member so that the filler can permeate the gap due to capillarity. Therefore, even if the plate member and/or the lid member is deformed by warpage or the like, the plate member and the lid member can be aligned with each other to be held so as to rectify the deformation, such as warpage, so that it is possible to allow the filler to permeate the gap between the sealing surface of the plate member and the lid member due to capillarity and it is possible to surely seal the portion surrounding the recessed portion of the plate member (the gap between the plate member and the lid member) with the filler.

According to the present invention, the spacers are provided between the plate member and the lid member to form the gap between the sealing surface of the plate member and the lid member so that the filler can permeate the gap due to capillarity. Therefore, even if the plate member and/or the lid member is deformed by warpage or the like, the plate member and the lid member can be aligned with each other to be held so as to rectify the deformation, such as warpage, so that it is possible to allow the filler to permeate the gap between the sealing surface of the plate member and the lid member due to capillarity and it is possible to surely seal the portion surrounding the recessed portion of the plate member (the gap between the plate member and the lid member) with the filler.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A plate assembly comprising:
a plate member having a recessed portion; and
a lid member mounted on said plate member to cover said recessed portion,
wherein said plate member has a bonded surface which is formed so as to surround said recessed portion, said lid member being bonded to said bonded surface with an adhesive which permeates between said plate member and said lid member around said recessed portion due to capillarity, and
said plate member has an adhesive relief portion which is formed around said bonded surface so as to be recessed from said bonded surface.

2. A plate assembly as set forth in claim 1, wherein said lid member has a through hole for injecting said adhesive into a space which is defined between said plate member and said lid member and which is communicated with said recessed portion.

3. A plate assembly as set forth in claim 1, wherein said lid member has a through hole for feeding a sample into said recessed portion.

4. A plate assembly as set forth in claim 1, wherein said lid member has an adhesive injecting hole which is open to a portion of said adhesive relief portion of said plate member in the vicinity of said bonded surface.

5. A plate assembly as set forth in claim 1, wherein said lid member has an adhesive injecting hole, at least a part of which is open to said adhesive relief portion of said plate member.

6. A plate assembly as set forth in claim 1, wherein said lid member has an adhesive injecting hole which is open to said bonded surface on the side of an end portion of said recessed portion.

7. A plate assembly as set forth in claim 1, wherein said bonded surface of said plate member has a spacer protrusion which contacts said lid member.

8. A plate assembly as set forth in claim 1, wherein said adhesive relief portion of said plate member has a spacer protrusion which contacts said lid member.

9. A plate assembly as set forth in claim 1, wherein each of said bonded surface of said plate member and said lid member has a spacer protrusion, and said spacer protrusion of said plate member contacts said spacer protrusion of said lid member.

10. A plate assembly as set forth in claim 1, wherein said plate member has a plurality of spacer protrusions which contact, and a distance between adjacent two of said plurality of spacer protrusions increases as a distance from said recessed portion increases.

11. A plate assembly comprising:
a plate member having a recessed portion; and
a lid member mounted on said plate member to cover said recessed portion,
wherein said plate member has a sealing surface which is formed so as to surround said recessed portion, said plate member having a lid member fixing surface which is separated from said sealing surface by a pass partition groove and which is fixed to said lid member, and a filler permeates between said sealing surface and said lid member due to capillarity.

12. A plate assembly as set forth in claim 11, wherein said filer is arranged between said sealing surface and said lid member.

13. A plate assembly as set forth in claim 11, wherein said lid member has a filler injecting hole, which is open to a portion of said pass partition groove of said plate member in the vicinity of said sealing surface, for injecting said filler into said pass partition groove.

14. A plate assembly as set forth in claim 11, wherein said lid member has a filler injecting hole, at least a part of which is open to said pass partition groove of said plate member, for injecting said filler into said pass partition groove.

15. A plate assembly as set forth in claim 11, wherein said lid member has a filler injecting hole, which is open to said sealing surface on the side of an end portion of said recessed portion of said plate member, for injecting said filler into said pass partition groove.

16. A plate assembly as set forth in claim 11, wherein said sealing surface of said plate member has a spacer protrusion which contacts said lid member.

17. A plate assembly as set forth in claim 11, wherein said lid member fixing surface of said plate member has a spacer protrusion which contacts.

18. A plate assembly as set forth in claim 11, wherein each of said sealing surface of said plate member and said lid member has a spacer protrusion, said spacer protrusion of said plate member contacting said spacer protrusion of said lid member.

19. A plate assembly as set forth in claim 11, wherein said plate member has a plurality of spacer protrusions which contact said lid member, and a distance between adjacent two of said plurality of spacer protrusions increases as a distance from said recessed portion increases.

20. A plate assembly as set forth in claim 1, wherein said lid member has a spacer protrusion which contacts said bonded surface of said plate member.

21. A plate assembly as set forth in claim 1, wherein said lid member has a spacer protrusion which contacts said adhesive relief portion of said plate member.

22. A plate assembly as set forth in claim 1, wherein said lid member has a plurality of spacer protrusions which contact said plate member, and a distance between adjacent two of said plurality of spacer protrusions increases as a distance from said recessed portion increases.

23. A plate assembly as set forth in claim 11, wherein said lid member has a spacer protrusion which contacts said sealing surface of said plate member.

24. A plate assembly as set forth in claim 11, wherein said lid member has a spacer protrusion which contacts said lid member fixing surface of said plate member.

25. A plate assembly as set forth in claim 11, wherein said lid member has a plurality of spacer protrusions which contact said plate member, and a distance between adjacent two of said plurality of spacer protrusions increases as a distance from said recessed portion increases.

* * * * *